United States Patent
Andreiko et al.

(10) Patent No.: US 10,204,414 B2
(45) Date of Patent: *Feb. 12, 2019

(54) INTEGRATION OF INTRA-ORAL IMAGERY AND VOLUMETRIC IMAGERY

(71) Applicant: ORMCO CORPORATION, Orange, CA (US)

(72) Inventors: Craig A. Andreiko, Alta Loma, CA (US); Robert F. Dillon, Bedford, NH (US); Bradley S. Carlson, Doylestown, PA (US)

(73) Assignee: ORMCO CORPORATION, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/905,528

(22) Filed: Feb. 26, 2018

(65) Prior Publication Data

US 2018/0182098 A1 Jun. 28, 2018

Related U.S. Application Data

(63) Continuation of application No. 14/847,651, filed on Sep. 8, 2015, now Pat. No. 9,904,999, which is a
(Continued)

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0088* (2013.01); *A61B 5/4547* (2013.01);
(Continued)

(58) Field of Classification Search
None
See application file for complete search history.

(56) References Cited

U.S. PATENT DOCUMENTS

| 7,063,532 B1 | 6/2006 | Jones et al. |
| 7,574,025 B2 | 8/2009 | Feldman |

(Continued)

FOREIGN PATENT DOCUMENTS

| WO | 2011154559 | 12/2011 |
| WO | 2012007003 A1 | 1/2012 |

OTHER PUBLICATIONS

European Search Report and Written Opinion for EP Application No. 13197241, dated Mar. 11, 2014, 8 pp.
(Continued)

*Primary Examiner* — Delomia L Gilliard
(74) *Attorney, Agent, or Firm* — Michael Best & Friedrich LLP

(57) ABSTRACT

Systems and methods are described for identifying a sub-gingival surface of a tooth in volumetric imagery data. Shape data is received from a surface scanner and volumetric imagery data is received from a volumetric imaging device. The shape data of the super-gingival portion of a first tooth is registered with the volumetric imagery data of the super-gingival portion of the first tooth to obtain a registration result. At least one criterion is then determined for detecting a surface of the first tooth in the volumetric imagery data of the super-gingival or the sub-gingival portion using the registration result. The surface of the sub-gingival portion of the first tooth is detected in the volumetric imagery data using the at least one criterion.

15 Claims, 19 Drawing Sheets

Related U.S. Application Data continuation of application No. 13/715,968, filed on Dec. 14, 2012, now Pat. No. 9,135,498.

(51) Int. Cl.

| | | |
|---|---|---|
| *A61B 6/14* | (2006.01) | |
| *G06T 3/00* | (2006.01) | |
| *G06K 9/00* | (2006.01) | |
| *G06T 17/10* | (2006.01) | |
| *A61B 6/03* | (2006.01) | |
| *G06T 7/11* | (2017.01) | |
| *G06T 7/187* | (2017.01) | |
| *G06F 19/00* | (2018.01) | |
| *A61B 5/107* | (2006.01) | |
| *A61B 6/00* | (2006.01) | |
| *A61B 90/00* | (2016.01) | |

(52) U.S. Cl.
CPC ............ *A61B 5/7425* (2013.01); *A61B 6/032* (2013.01); *A61B 6/14* (2013.01); *A61B 6/5247* (2013.01); *G06F 19/00* (2013.01); *G06K 9/00201* (2013.01); *G06T 3/0068* (2013.01); *G06T 7/11* (2017.01); *G06T 7/187* (2017.01); *G06T 17/10* (2013.01); *A61B 5/1077* (2013.01); *A61B 5/4504* (2013.01); *A61B 5/682* (2013.01); *A61B 5/6814* (2013.01); *A61B 5/7445* (2013.01); *A61B 6/4085* (2013.01); *A61B 2090/365* (2016.02); *A61B 2090/3762* (2016.02); *G06T 2200/04* (2013.01); *G06T 2207/30036* (2013.01)

(56) References Cited

U.S. PATENT DOCUMENTS

| | | | |
|---|---|---|---|
| 8,199,988 B2 | 6/2012 | Marshall et al. | |
| 2002/0037489 A1* | 3/2002 | Jones | A61C 7/00 433/24 |
| 2004/0175671 A1* | 9/2004 | Jones | A61C 7/00 433/24 |
| 2006/0127854 A1* | 6/2006 | Wen | A61C 7/00 433/213 |
| 2007/0160957 A1 | 7/2007 | Wen | |
| 2009/0129639 A1 | 5/2009 | Ortega et al. | |
| 2009/0148809 A1 | 6/2009 | Kuo et al. | |
| 2009/0316966 A1* | 12/2009 | Marshall | A61B 6/5217 382/128 |
| 2010/0124367 A1 | 5/2010 | Cizek | |
| 2011/0008751 A1 | 1/2011 | Pettersson | |
| 2011/0255765 A1 | 10/2011 | Carlson et al. | |
| 2011/0268327 A1* | 11/2011 | Getto | G06T 7/0024 382/128 |
| 2012/0015316 A1 | 1/2012 | Sachdeva et al. | |
| 2012/0214121 A1* | 8/2012 | Greenberg | A61B 5/0088 433/24 |
| 2012/0282567 A1 | 11/2012 | Nilsson | |
| 2014/0227655 A1 | 8/2014 | Andreiko et al. | |
| 2015/0297149 A1* | 10/2015 | Park | A61B 6/14 345/419 |
| 2016/0331463 A1* | 11/2016 | Notzli | G06T 19/20 |

OTHER PUBLICATIONS

Response to EP Search Report and Written Opinion for EP Application No. 13197241, dated Dec. 17, 2014, 9 pp.
Office Action 1 for U.S. Appl. No. 13/765,600, dated Apr. 17, 2014, 7 pp.
Response to Office Action 1 for U.S. Appl. No. 13/765,600, dated Jul. 31, 2014, 9 pp.
Final Office Action 1 for U.S. Appl. No. 13/765,600, dated Nov. 20, 2014, 11 pp.
Response to Final Office Action 1 for U.S. Appl. No. 13/765,600, dated Mar. 20, 2015, 9 pp.
Office Action 2 for U.S. Appl. No. 13/765,600, dated Apr. 6, 2015, 6 pp.
Response to Office Action 2 for U.S. Appl. No. 13/765,600, dated Aug. 31, 2015, 9 pp.
European Patent Office Action for Application No. 13197241.6 dated Nov. 17, 2015 (5 pages).
Japanese Patent Office Action for Application No. 2013-257971 dated Oct. 6, 2017 (6 pages with English Translation).

* cited by examiner

2300

2302 — RECEIVING SHAPE DATA OF A PATIENT'S CROWN AND VOLUMETRIC IMAGERY OF THE PATIENT'S TOOTH

2304 — DETERMINING ELEMENTS THAT REPRESENT ONE OR MORE CROWNS IN THE SHAPE DATA

2306 — USING A COMPUTATIONAL DEVICE TO REGISTER THE ELEMENTS WITH CORRESPONDING VOXELS OF THE VOLUMETRIC IMAGERY

2402 — RECEIVING SHAPE DATA OF A PATIENT'S CROWN AND VOLUMETRIC IMAGERY

2404 — DETERMINING ELEMENTS THAT REPRESENT ONE OR MORE CROWNS IN THE SHAPE DATA

2406 — REGISTERING THE ELEMENTS WITH CORRESPONDING VOXELS OF THE VOLUMETRIC IMAGERY, AND DETERMINING VOLUMETRIC COORDINATES AND RADIODENSITIES TO DETERMINE A TOOTH SHAPE

FIG. 24

INTEGRATION OF INTRA-ORAL IMAGERY AND VOLUMETRIC IMAGERY

RELATED APPLICATIONS

This application is a continuation of U.S. patent application Ser. No. 14/847,651, filed on Sep. 8, 2015, which is a continuation of U.S. patent application Ser. No. 13/715,968, filed on Dec. 14, 2012 and entitled "INTEGRATION OF INTRA-ORAL IMAGERY AND VOLUMETRIC IMAGERY," the entire contents of which are incorporated herein by reference.

FIELD

The disclosure relates to a system, method, and computer readable storage medium for the integration of intra-oral imagery and volumetric imagery.

BACKGROUND

An intra-oral imaging system is a diagnostic equipment that allows a dental practitioner to see the inside of a patient's mouth and display the topographical characteristics of teeth on a display monitor. Certain three-dimensional (3D) intra-oral imagers may be comprised of an intra-oral camera with a light source. The 3D intra-oral imager may be inserted into the oral cavity of a patient by a dental practitioner. After insertion of the intra-oral imager into the oral cavity, the dental practitioner may capture images of visible parts of the teeth and the gingivae. The 3D intra-oral imager may be fabricated in the form of a slender rod that is referred to as a wand or a handpiece. The wand may be approximately the size of a dental mirror with a handle that is used in dentistry. The wand may have a built-in light source and a video camera that may achieve an imaging magnification, ranging in scale from ¹⁄₁₀ to 40 times or more. This allows the dental practitioner to discover certain types of details and defects of the teeth and gums. The images captured by the intra-oral camera may be displayed on a display monitor and may be transmitted to a computational device.

Cone beam computed tomography (CBCT) involves the use of a rotating CBCT scanner, combined with a digital computer, to obtain images of the teeth and surrounding bone structure, soft tissue, muscle, blood vessels, etc. CBCT may be used in a dental practitioner's office to generate cross-sectional images of teeth and the surrounding bone structure, soft tissue, muscle, blood vessels, etc. During a CBCT scan, the CBCT scanner rotates around the patient's head and may obtain hundreds of distinct CBCT images that may be referred to as CBCT imagery. The CBCT imagery may be transmitted to a computational device. The CBCT imagery may be analyzed to generate three-dimensional anatomical data. The three-dimensional anatomical data can then be manipulated and visualized with specialized software to allow for cephalometric analysis of the CBCT imagery.

SUMMARY

Provided are a system, method, and computer readable storage medium in which shape data of a patient's crown and volumetric imagery of the patient's tooth are received. A determination is made of elements that represent one or more crowns in the shape data. A computational device is used to register the elements with corresponding voxels of the volumetric imagery.

In additional embodiments, a determination is made of volumetric coordinates and radiodensities corresponding to the voxels.

In further embodiments, at least one of the patient's root is determined via region growing from starting locations that include one or more of the determined volumetric coordinates and radiodensities at the voxels.

In further embodiments, the region growing is performed by identifying adjacent voxels that possess correlated radiodensities along a longitudinal direction of the patient's tooth.

In certain embodiments, the shape data of the patient's crown is obtained via an impression, a plaster model or an intra-oral scan. The volumetric imagery is selected from a group consisting of tomographic imagery, ultrasonic imagery, cone beam computed tomography (CBCT) imagery and magnetic resonance imagery (MRI).

In further embodiments, the elements are vectors, and boundaries in the shape data correspond to the one or more crowns. The one or more crowns are represented by a plurality of limited length vectors and the volumetric imagery is represented by a plurality of voxels. Intersections of the plurality of limited length vectors and the plurality of voxels are determined subsequent to the registering.

In further embodiments, the volumetric imagery is represented by a first plurality of voxels, and the one or more crowns are represented by a second plurality of voxels. The first plurality of voxels and the second plurality of voxels are registered.

In further embodiments, one or more crowns are determined in the shape data via segmentation of the shape data.

In yet further embodiments, the shape data is from intra-oral imagery, and the volumetric imagery is cone beam computed tomography (CBCT) imagery. The intra-oral imagery is of a higher precision than the CBCT imagery. The volumetric imagery includes both roots and crowns of teeth. The intra-oral imagery includes at least the crowns of the teeth but does not include an entirety of the roots of the teeth.

In still further embodiments, a determination is made of an area of interest in the intra-oral imagery, wherein the area of interest corresponds to a location of the one or more crowns determined in the intra-oral imagery. An extraction is made within the volumetric imagery of the area of interest to reduce a size of the volumetric imagery.

Provided also are a method, system, and a computer readable storage medium in which a computational device receives shape data of a patient's crown and volumetric imagery. A determination is made of elements that represent one or more crowns in the shape data. The elements are registered with corresponding voxels of the volumetric imagery. Volumetric coordinates and radiodensities are determined to determine a tooth shape.

In additional embodiments, determining the tooth shape comprises filling missing or degraded data in the shape data.

In yet additional embodiments, determining the tooth shape comprises filling missing or degraded data in the volumetric imagery.

In further embodiments, the tooth shape is determined with greater precision in comparison to the received volumetric imagery, and the tooth shape is determined with greater precision with usage of lesser radiation. At least one of the patient's root is determined via region growing from starting locations that include one or more of determined volumetric coordinates and radiodensities at the voxels.

In yet further embodiments, the volumetric imagery is represented by a first plurality of voxels. The one or more crowns are represented by vectors or a second plurality of voxels. The first plurality of voxels are registered to the vectors or the second plurality of voxels.

Provided also are a method, system, and a computer readable storage medium in which for improving shape data of a patient's crown, the shape data of the patient's crown is registered with volumetric data of the patient's tooth.

Other aspects of the invention will become apparent by consideration of the detailed description and accompanying drawings.

BRIEF DESCRIPTION OF THE DRAWINGS

Referring now to the drawings in which like reference numbers represent corresponding parts throughout:

FIG. 23 illustrates a flowchart that shows registration of elements in shape data of a patient's crown with corresponding voxels in volumetric imagery, in accordance with certain embodiments;

FIG. 24 illustrates a flowchart that shows registration of elements in shape data of a patient's crown with corresponding voxels in volumetric imagery to determine tooth shape, in accordance with certain embodiments.

DETAILED DESCRIPTION

In the following description, reference is made to the accompanying drawings which form a part hereof and which illustrate several embodiments. It is understood that other embodiments may be utilized and structural and operational changes may be made.

Intra-Oral Imagery and CBCT Imagery

Generally intra-oral images are of a significantly higher precision in comparison to CBCT images. Furthermore, CBCT data can be noisy. Also, the use of CBCT results in ionizing radiation to the patient and it is best to use CBCT systems with as little radiation as possible.

In certain embodiments, a computational device receives shape data of a patient's crown and volumetric imagery of the patient's tooth. The shape data may be generated from intra-oral images and may correspond to the surface data of the patient's crown. The volumetric imagery may comprise CBCT imagery or other types of volumetric imagery. A determination is made of voxels that represent one or more crowns in the shape data. The voxels in the shape data are registered with corresponding voxels of the volumetric imagery.

In certain embodiments, segmented crowns determined from intra-oral imagery are registered to voxels of CBCT images. This allows more accurate determination of the boundary between the crown and the root of a tooth in the CBCT data. It may be noted that without the use of the intra-oral imagery the boundary between the crown and the root of a tooth may be fuzzy (i.e., not clear or indistinct) in CBCT imagery.

In certain embodiments, the surface scan data of an intra-oral imaging system is registered to the volumetric data obtained from a CBCT system. The 3-D coordinates of the crown boundaries that are found in the intra-oral imagery are mapped to the voxels of the CBCT imagery to determine the boundary between roots and crowns at a sub-voxel levels of accuracy in the CBCT imagery. As a result, the roots can be extracted, even from noisy CBCT scan data.

In additional embodiments, holes in intra-oral imagery may be filled in by integrating CBCT imagery with intra-oral imagery.

Exemplary Embodiments

Figure 1:
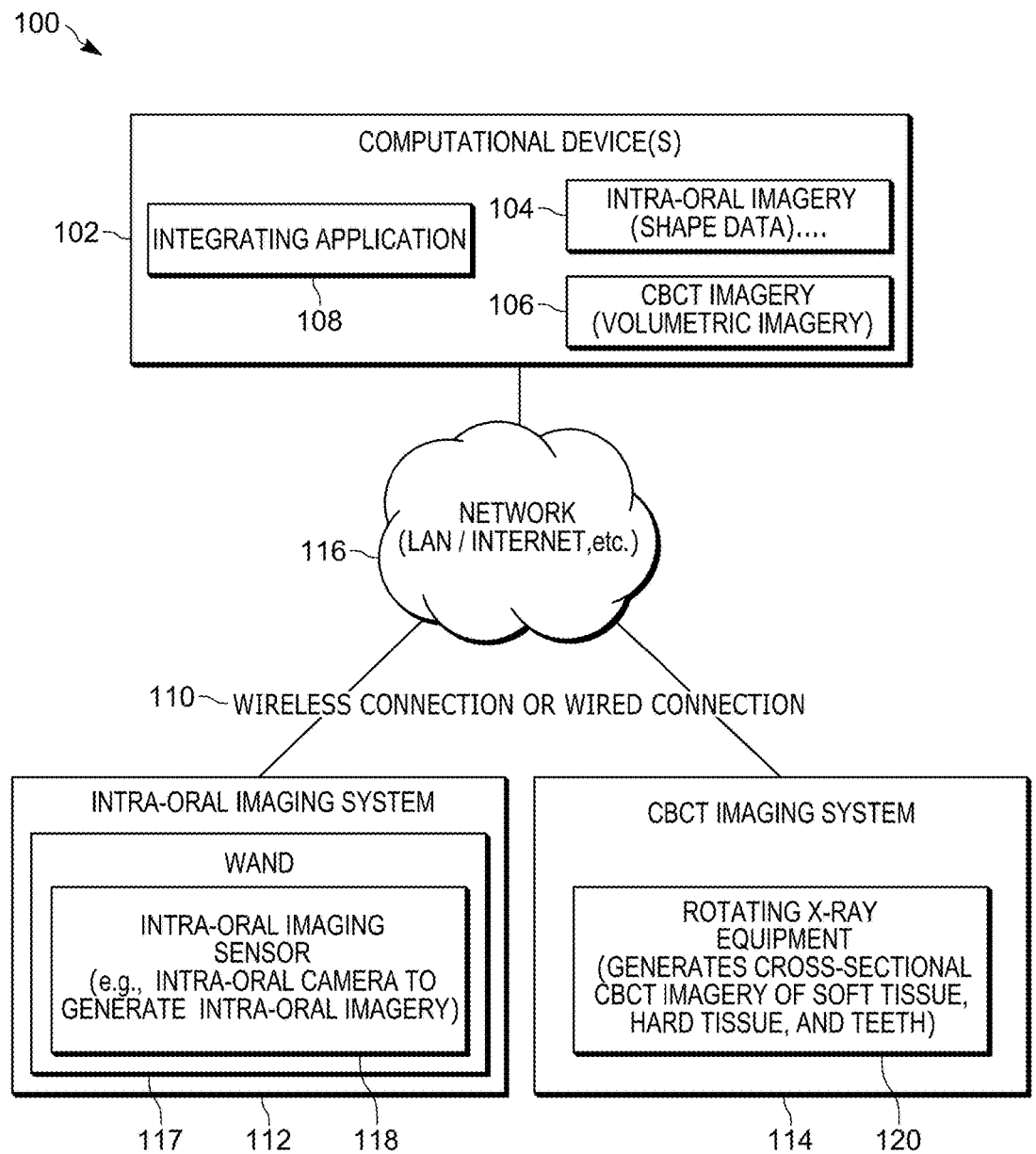
FIG. 1 illustrates a block diagram of a computing and imaging environment that includes a computational device that integrates intra-oral imagery and volumetric imagery, such as CBCT imagery, in accordance with certain embodiments.

FIG. 1 illustrates a block diagram of a computing and imaging environment 100 that includes a computational device 102 that integrates intra-oral imagery 104 and CBCT imagery 106, in accordance with certain embodiments. The computational device 102 may include any suitable computational device such as a personal computer, a server computer, a mini computer, a mainframe computer, a blade computer, a tablet computer, a touchscreen computing device, a telephony device, a cell phone, a mobile computational device, a dental equipment having a processor, etc., and in certain embodiments the computational device 102 may provide web services or cloud computing services. In certain alternative embodiments, more than one computational device may be used for storing data or performing the operations performed by the computational device 102.

The intra-oral imagery 104 provides surface data of a patient's crown and the CBCT imagery 106 provides volumetric imagery of a patient's tooth, where the tooth may include both the crown and the root. In alternative embodiments, the surface data of the patient's crown may be provided by imagery that is different from intra-oral imagery, and the volumetric imagery may be provided by other types of tomographic imagery, ultrasonic imagery, magnetic resonance imagery (MRI), etc. The volumetric imagery comprises three dimensional imagery and may be represented via voxels.

The computational device 102 may include an integrating application 108, implemented in certain embodiments in software, hardware, firmware or any combination thereof. The integrating application 108 integrates the intra-oral imagery 104 and the CBCT imagery 106 to provide additional functionalities that are not found in either the intra-oral imagery 104 or the CBCT imagery 106 when they are not integrated.

The computational device 102 is coupled via one or more wired or wireless connections 110 to an intra-oral imaging system 112 and a CBCT imaging system 114, over a network 116. In certain embodiments, the network 116 may comprise a local area network, the Internet, and intranet, a storage are network, or any other suitable network.

The intra-oral imaging system 112 may include a wand 117 having an intra-oral imaging sensor 118, where in certain embodiments the intra-oral imaging sensor 118 is an intra-oral camera that generates intra-oral imagery of the oral cavity of a patient. The CBCT imaging system 114 may include a rotating X-ray equipment 120 that generates cross-sectional CBCT imagery of the soft tissue, hard tissue, teeth, etc. of a patient.

Therefore, FIG. 1 illustrates certain embodiments in which an integrating application 108 that executes in the computational device 102 integrates intra-oral imagery 104 generated by an intra-oral imaging system 112 with CBCT imagery 106 generated by a CBCT imaging system 114. In certain additional embodiments, the intra-oral imagery 104 and the CBCT imagery 106 may be stored in a storage medium (e.g., a disk drive, a floppy drive, a pen drive, a solid state device, an optical drive, etc.), and the storage medium may be coupled to the computational device 102 for reading and processing by the integrating application 108.

Figure 2:
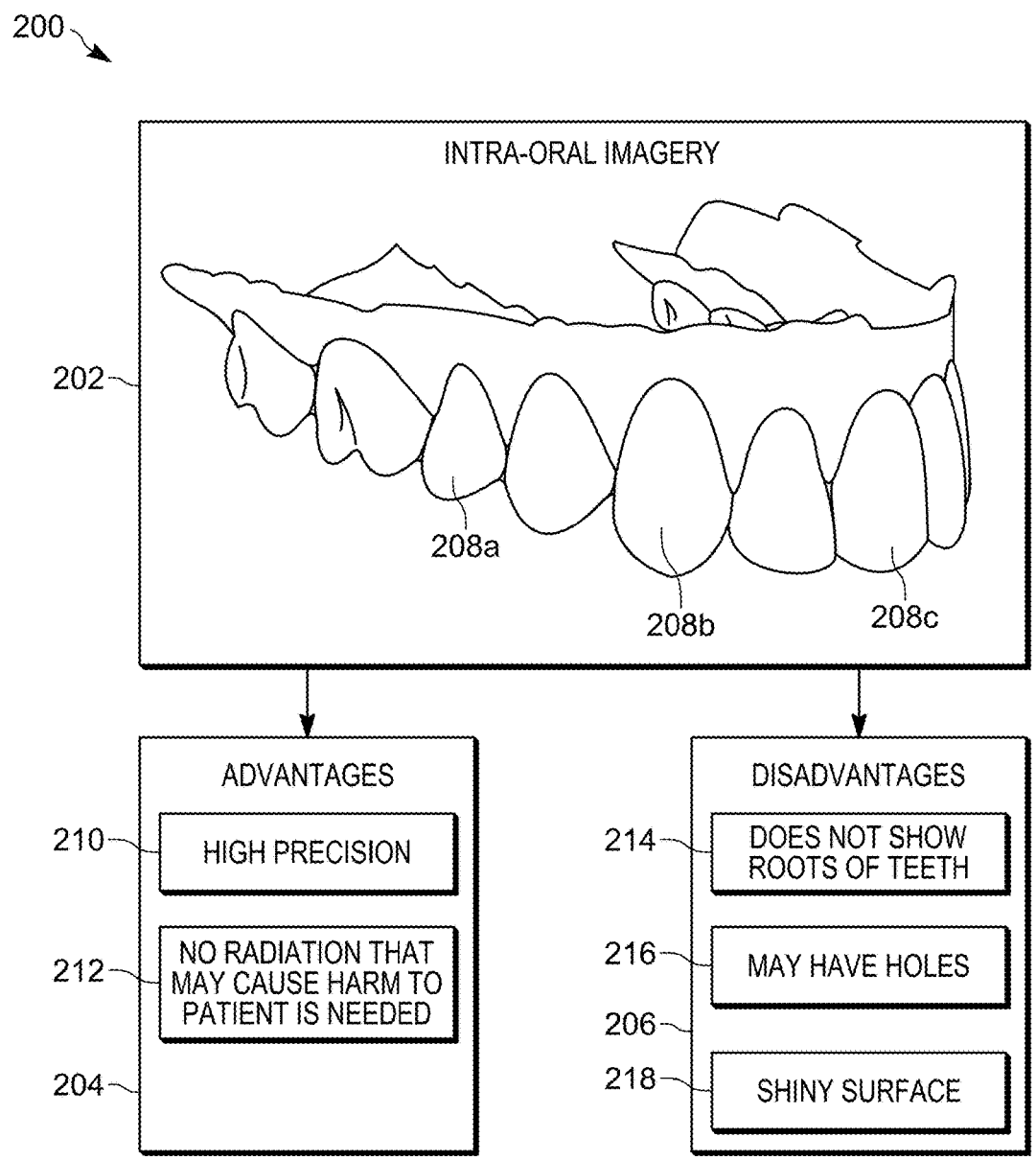
FIG. 2 illustrates a diagram in which an exemplary intra-oral imagery and advantages and disadvantages of intra-oral imagery are shown, in accordance with certain embodiments.

FIG. 2 illustrates a diagram 200 in which an exemplary intra-oral imagery 202 is shown, in accordance with certain embodiments. Certain exemplary advantages 204 and certain exemplary disadvantages 206 of the intra-oral imagery 202 are also shown, in accordance with certain embodiments.

The intra-oral imagery 206 shows exemplary crowns (e.g., crowns 208 a, 208 b, 208 c) in the upper arch of the oral cavity of a patient, where the intra-oral imagery 206 may have been acquired via the intra-oral imaging system 112. The crown is the portion of the tooth that may be visually seen, and the root is the portion of the tooth that is hidden under the gum.

FIG. 2 shows that the intra-oral imagery is typically of a high precision 210 in comparison with CBCT imagery. Additionally, no radiation that may cause harm to the patient (shown via reference numeral 212) is needed in acquiring the intra-oral imagery 202. However, the intra-oral imagery 202 does not show the roots of teeth (reference numeral 214) and may have holes 216, where a hole is a portion of the tooth that is not visible in intra-oral imagery. Holes may arise because of malocclusions or for other reasons. While, small and medium sized holes may be filled (i.e., the hole is substituted via a simulated surface generated programmatically via the computational device 102) by analyzing the intra-oral imagery 202, larger holes (i.e. holes that exceed certain dimensions) may not be filled by just using data found in intra-oral imagery. Additionally, shiny surfaces of crowns may generate poor quality intra-oral imagery (reference numeral 218).

Therefore, FIG. 2 illustrates certain embodiments in which intra-oral imagery may have holes and do not show the entirety of the roots of teeth.

Figure 3:
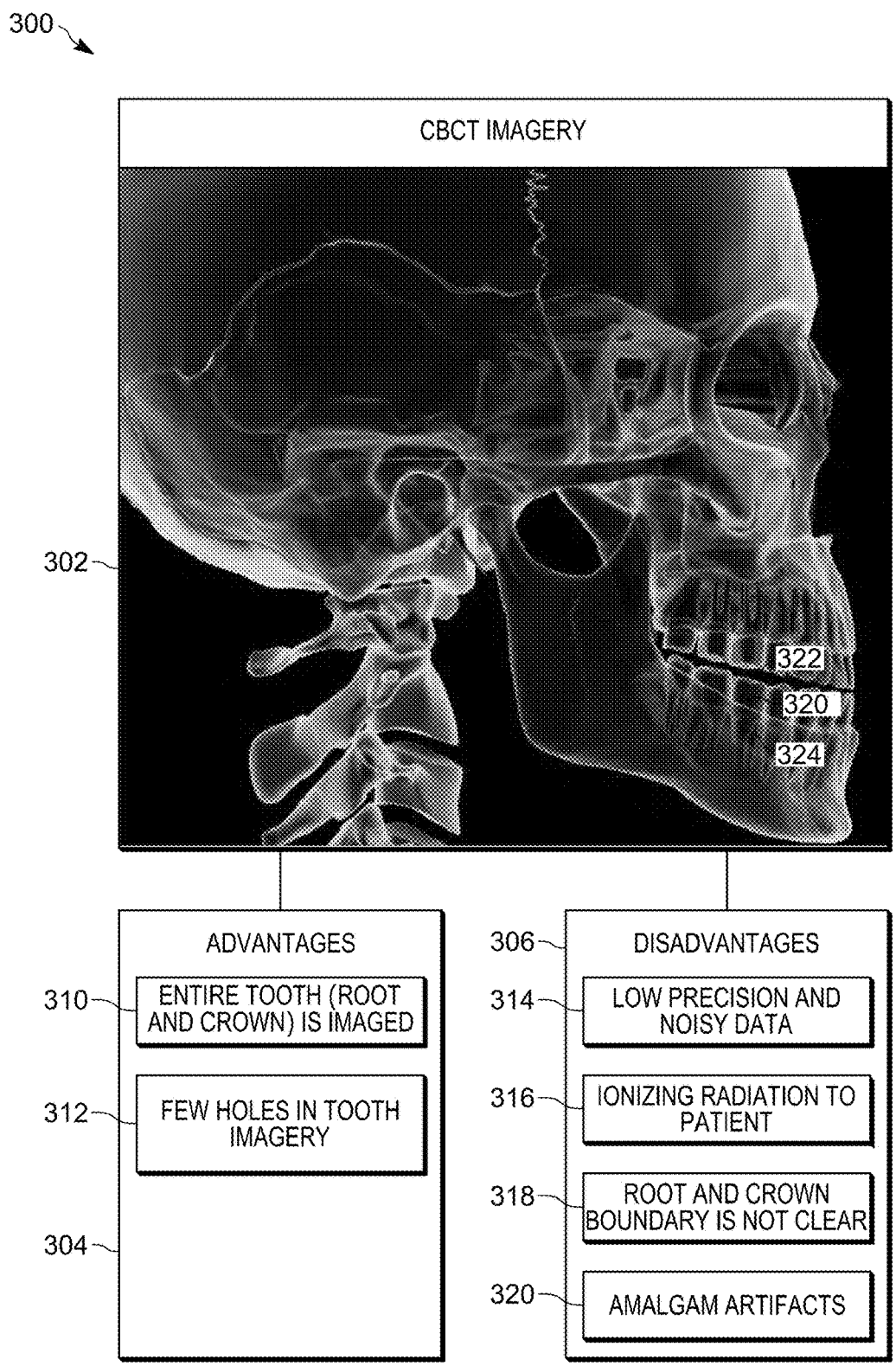
FIG. 3 illustrates a diagram in which an exemplary CBCT imagery and advantages and disadvantages of CBCT are shown, in accordance with certain embodiments.

FIG. 3 illustrates a diagram 300 in which an exemplary CBCT imagery 302, and certain advantages 304 and certain disadvantages 306 of CBCT imagery are shown, in accordance with certain embodiments.

In the CBCT imagery the entire tooth (i.e., the root and the crown) is imaged (reference number 310) and there are few holes (reference number 312). The few holes that exist may be caused by artifacts as a result of amalgam fillings on tooth (reference numeral 320). However, the CBCT images may be of a lower precision and may be more noisy in comparison to intra-oral imagery (reference numeral 314). There is a potential for ionizing radiation to the patient in the acquisition of CBCT imagery (reference numeral 316) unlike in intra-oral imagery in which there is no ionizing radiation in the acquisition process. Furthermore, while the complete tooth is imaged in CBCT imagery, the boundary between the root and the crown may not be clear (reference numeral 318) as may be seen (reference numeral 320) in the exemplary CBCT imagery 302. The fuzzy and indistinct boundary 320 between the crown 322 and the root 324 may be caused by varying radiodensities during the process of acquiring CBCT images. In certain embodiments, motion of the patient may generate inferior quality CBCT imagery.

Therefore, FIG. 3 illustrates certain embodiments in which CBCT images may have low precision and have noisy data with the boundary between the root and crown not being clearly demarcated.

Figure 4:
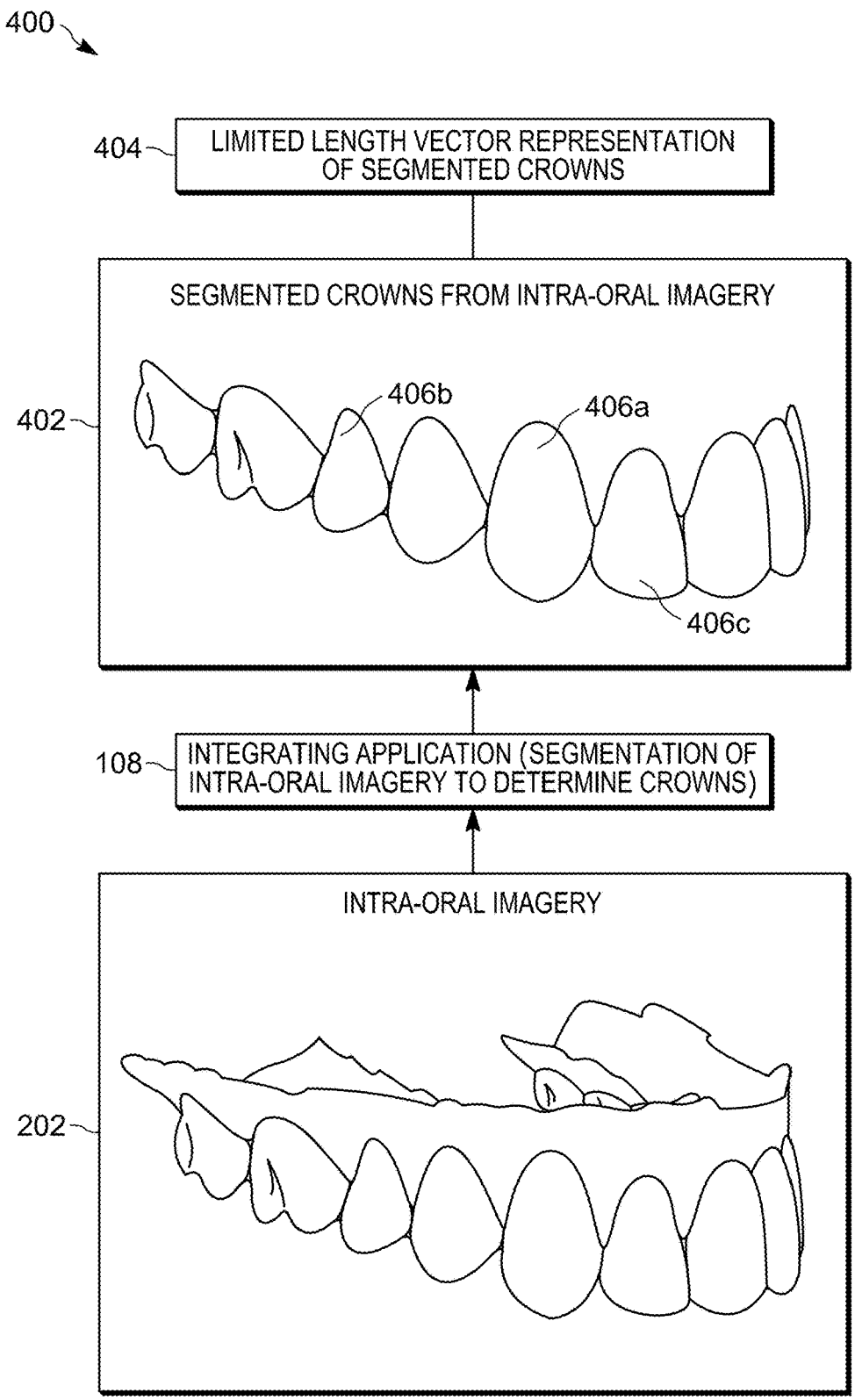
FIG. 4 illustrates a diagram that shows how an intra-oral imagery is segmented to determine crowns represented via limited length vectors, in accordance with certain embodiments.

FIG. 4 illustrates a diagram 400 that shows how an intra-oral imagery 202 is segmented to determine crowns 402 represented via limited length vectors 404, in accordance with certain embodiments. The segmentation of the intra-oral imagery 202 to determine crowns 402 may be performed via the integrating application 108 that executes in the computational device 102. Exemplary segmented crowns are shown via reference numerals 406 a, 406 b, 406 c. The segmented crowns are of a high resolution and show clearly defined edges and are represented via limited length vectors 404. A vector has a direction and magnitude in three-dimensional space. A limited length vector is a vector whose length is limited. In other embodiments, the segmented crowns may be represented via data structures or mathematical representations that are different from limited length vectors 404.

Therefore, FIG. 4 illustrates certain embodiments in which intra-oral imagery is segmented to determine crowns represented via limited length vectors.

Figure 5:
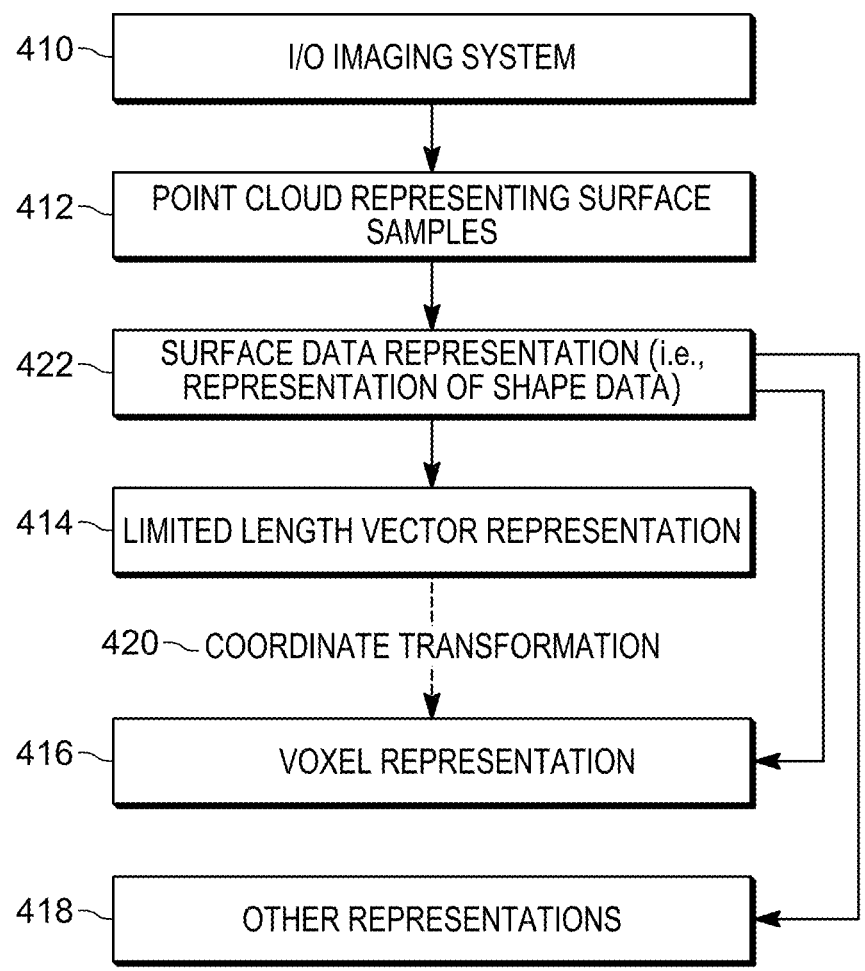
FIG. 5 illustrates a diagram that shows how the surface data obtained via intra-oral imagery may be represented via limited length vectors or voxels, in accordance with certain embodiments.

FIG. 5 illustrates a diagram that shows how an intra-oral imaging system 410 scans the inside of a patient's mouth and generates surface samples of the crowns of a patient's teeth, where the aggregated surface samples may be referred to as a point cloud 412.

The point cloud 412 may processed by the integrating application 108 executing the computational device 102 to represent the surface of the crowns. The crown of the tooth is a solid object, and the surfaces of the crown correspond to the boundaries of the solid object. The crown surface may be represented by a surface mesh of node points connected by triangles, quadrilaterals or via different types of polygon meshes. In alternative embodiments, a solid mesh may also be used to represent the crown surface. The process of creating the mesh is referred to as tessellation.

In certain embodiments, the surface corresponding to the crown is represented in three dimensional space via limited length vectors 414 or via voxels 416 or via other data structures 418. The voxels 416 correspond to three-dimensional points on the surface of a crown. In certain embodiments, the limited length vectors 414 may be converted to vowel representation via appropriate three dimensional coordinate transformations 420. The limited length vectors 414 may correspond to the sides of the different types of polygon meshes (e.g., triangles, quadrilaterals, etc.) in the surface representation of the crown.

Therefore, FIG. 5 illustrates certain embodiments in which intra-oral imagery is processed to determine crowns represented via limited length vectors or via voxels. The limited length vectors or voxels correspond to a surface data representation 422 of the crown. Surface data may also be referred to as shape data.

Figure 6:
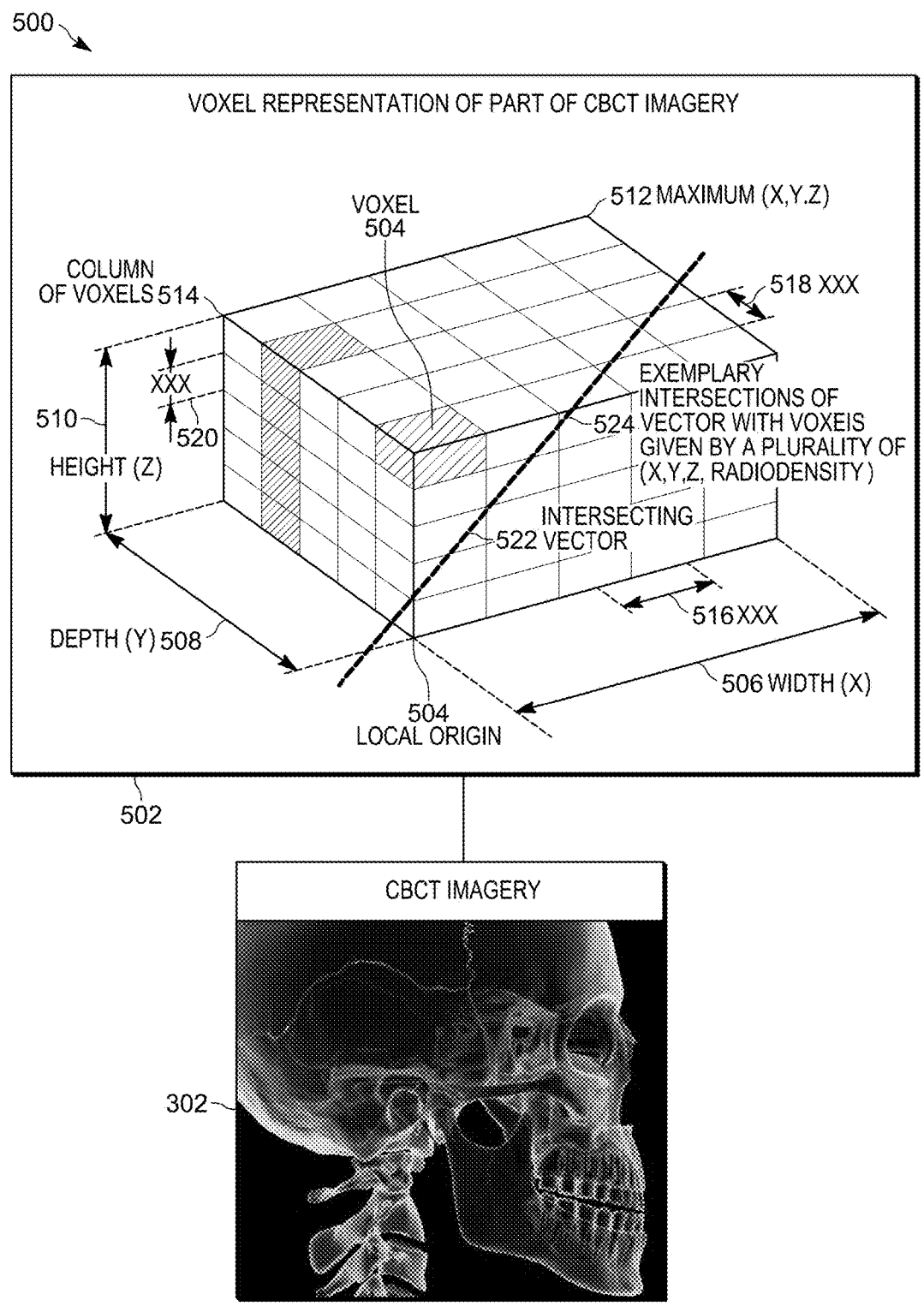
FIG. 6 illustrates a diagram that shows how voxels represent CBCT imagery, in accordance with certain embodiments.

FIG. 6 illustrates a diagram 500 that shows how voxels 502 represent CBCT imagery 302, in accordance with certain embodiments. A voxel (e.g., voxel 504) is a volumetric pixel that is a digital representation of radiodensity in a volumetric framework corresponding to the CBCT imagery 302. The radio density may be measured in the Hounsfield scale. In FIG. 6 an exemplary voxel representation 502 of part of the CBCT imagery 302 is shown.

The voxel representation 502 has a local origin 504, with X, Y, Z coordinates representing width, depth, and height respectively (shown via reference numerals 506, 508, 510). The coordinate of the voxel where the X, Y, Z values are maximum are shown via the reference numeral 512. An exemplary voxel 504 and an illustrative column of voxels 514 are also shown. Each voxel has a volume defined by the dimensions shown via reference numerals 516, 518, 520.

In certain embodiments, limited length vectors of intra-oral imagery are registered to the voxel representation of the CBCT imagery, to determine where the limited length vectors intersect the voxels of the CBCT imagery. In an exemplary embodiments, an intersecting limited length vector 522 is shown to intersect the voxels of the CBCT imagery at various voxels, wherein at least one voxel 524 at which the intersection takes place has a volumetric coordinate of (X,Y,Z) with an associated radiodensity.

Therefore, FIG. 6 illustrates certain embodiments in which CBCT imagery is represented via voxels. The limited length vectors of the intra-oral imagery intersects the voxels of the CBCT imagery when both are placed in the same coordinate system, wherein each intersection has a X,Y,Z coordinate and a radiodensity. In certain embodiments, the limited length vectors may be one or more of the sides of triangulated tessellations used to represent shape data. The limited length vectors may be chained in shape representations.

Figure 7:
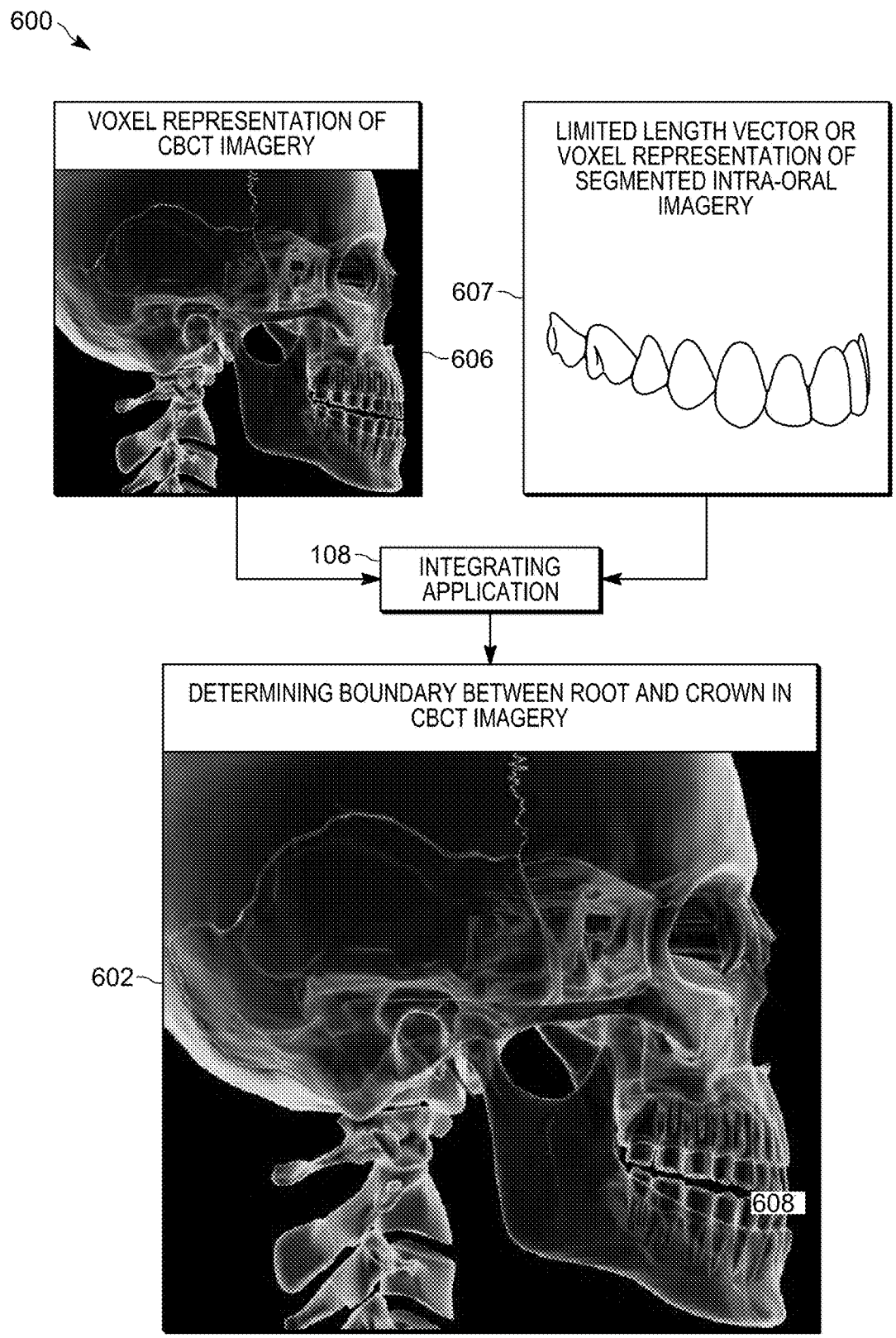
FIG. 7 illustrates a diagram that shows how the boundary between root and crown is determined in CBCT imagery by integrating intra-oral imagery with CBCT imagery, in accordance with certain embodiments.

FIG. 7 illustrates a diagram 600 that shows how the boundary between root and crown is determined in CBCT imagery by integrating intra-oral imagery with CBCT imagery, in accordance with certain embodiments. In certain embodiments, the voxel representation 606 of CBCT imagery is integrated (via the integrating application 108) with the limited length vector representation or voxel representation 607 of the intra-oral imagery to overlay the high resolution clearly segmented crowns of the intra-oral imagery on the low resolution fuzzy crowns of the CBCT imagery (as shown via reference numeral 608), to clearly demarcate the boundary between roots and crowns in the CBCT imagery 602. In certain embodiments the integration of CBCT imagery and intra-oral imagery results in a type of filtration operation that sharpens the CBCT imagery to determine the boundary between roots and crowns.

Therefore, FIG. 7 illustrates certain embodiments in which CBCT imagery is augmented with data from intra-oral imagery to determine the boundary between roots and crowns with a greater degree of accuracy in comparison to using the CBCT imagery alone. As a result of the augmentation, high precision crowns and low precision roots are obtained.

Figure 8:
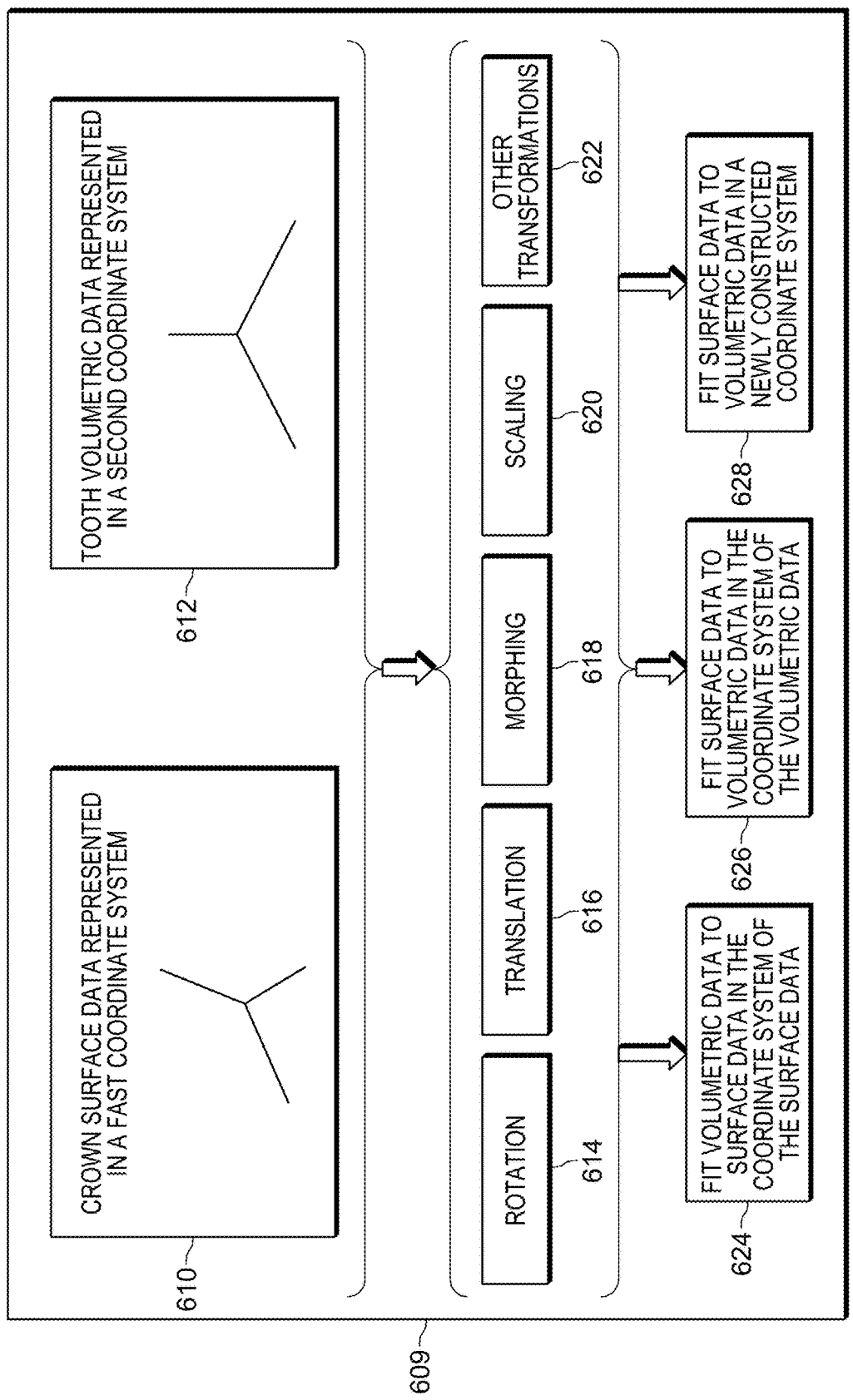
FIG. 8 illustrates a diagram that shows how surface data and volumetric data are fitted to each other, in accordance with certain embodiments.

FIG. 8 illustrates a diagram 609 that shows how surface data and volumetric data are fitted to each other, in accordance with certain embodiments. In certain embodiments, the surface data (i.e., the crown surface data) may be represented with reference to a first coordinate system (shown via reference numeral 610) The volumetric data that represents the tooth may be represented in a second coordinate system (shown via reference numeral 612).

In certain embodiments one or both of the crown surface data and the tooth volumetric data may have to be rotated 614, translated 616, morphed 618, scaled 620, or made to undergo other transformations 622 to appropriately overlap the crown surface data and the tooth volumetric data in a single unified coordinate system. For example, in certain embodiments the tooth volumetric data is fitted to the crown surface data in the coordinate system of the tooth surface data by appropriate rotations, translations, morphing, scaling, etc., of the tooth volumetric data (as shown via reference numeral 624). In other embodiments, crown surface data is fitted to the tooth volumetric data in the coordinate system of the tooth volumetric data by appropriate rotations, translations, morphing, scaling, etc., of the crown surface data (as shown via reference numeral 626). In other embodiments, both the crown surface data and the tooth volumetric data may undergo rotations, translations, morphing, scaling, etc. to fit the crown surface data and tooth volumetric data in a new coordinate system (as shown via reference numeral 628).

Figure 9:
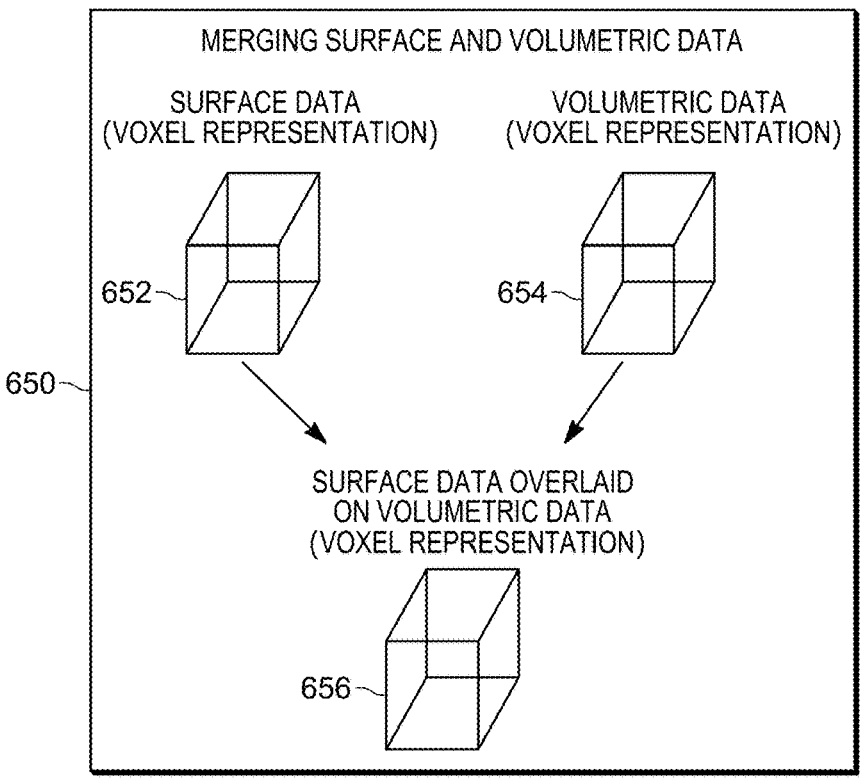
FIG. 9 illustrates a diagram that shows how surface data of the crown is merged to volumetric data of the tooth, in accordance with certain embodiments.

FIG. 9 illustrates a diagram 650 that shows how surface data of the crown is merged to volumetric data of the tooth, in accordance with certain embodiments. An empty cube of voxels in the three dimensional space is populated with the shape data of a crown. As a result, the surface data of the crown is represented via voxels of a three dimensional space 652.

The three dimensional space 652 with surface data is overlaid on the three dimensional space 654 that has the volumetric representation of the tooth, to generate the overlay of the surface data on the volumetric data shown in the three dimensional space 656. The fitting of the surface data to the volumetric data may be performed via an iterative closest point (ICP) registration. ICP may fit points in surface data to the points in volumetric data. In certain embodiment, the fitting may minimize the sum of square errors with the closest volumetric data points and surface data points. In certain embodiments, the limited length vectors of the surface data are represented as voxels prior to performing the ICP registration.

The anatomy of brackets, wires, filling or other features on the tooth may often assist in properly registering the surface data to the volumetric data. The registration may in various embodiments be performed via optimization techniques, such as simulated annealing, correlation techniques, dynamic programming, linear programming etc.

In certain embodiments a multiplicity of representations of the same object obtained by CBCT, magnetic resonance imagery (MRI), ultrasound imagery, intra-oral imagery based surface data, etc., may be registered to generate a better representation of a crown in comparison to embodiments that do not use data from the multiplicity of representations.

Figure 10:
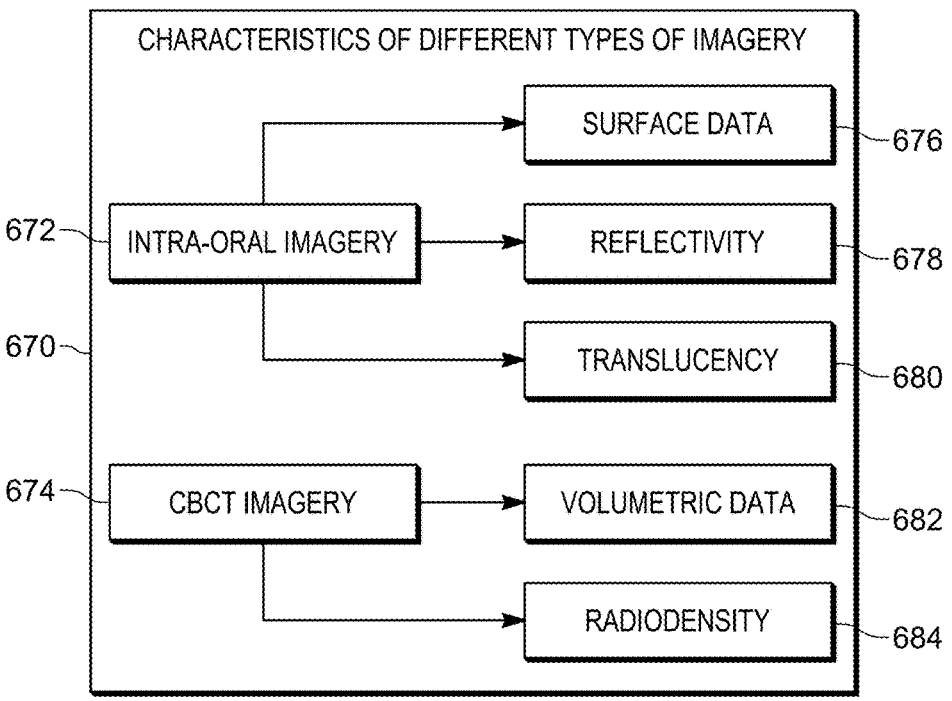
FIG. 10 illustrates a diagram that shows characteristics of different types of imagery, in accordance with certain embodiments.

FIG. 10 illustrates a diagram 670 that shows characteristics of different types of imagery, in accordance with certain embodiments. The intra-oral imagery 672 may provide not only the surface data 676 but may also be processed to provide information on reflectivity 678 and translucency 680 of the surface of the objects that are imaged. For example, the reflectivity and the translucency of the crown may be different from that the gingiva, and the intra-oral imagery 672 may be processed to distinguish the crown from the gingiva based on the reflectivity and the translucency differences and the segmentation of the crown may be improved by incorporating such additional information. In certain embodiments where interferometry fringe patterns are used for capturing the intra-oral imagery the reflectivity and translucency information may be generated with greater precision in comparison to embodiments where such fringe patterns are not used.

In certain embodiments, the volumetric data 682 and the radiodensity information 684 corresponding to the CBCT imagery 674 may be used in association with the surface data 676, reflectivity information 678 and translucency information 680 of the intra-oral imagery 672 to provide additional cues for performing the registration of the surface data 676 and the volumetric data 682. Ray tracing mechanisms may also be used for simulating a wide variety of optical effects, such as reflection and refraction, scattering, and dispersion phenomena (such as chromatic aberration) for improving the quality of the different types of images and for registration.

Figure 11:
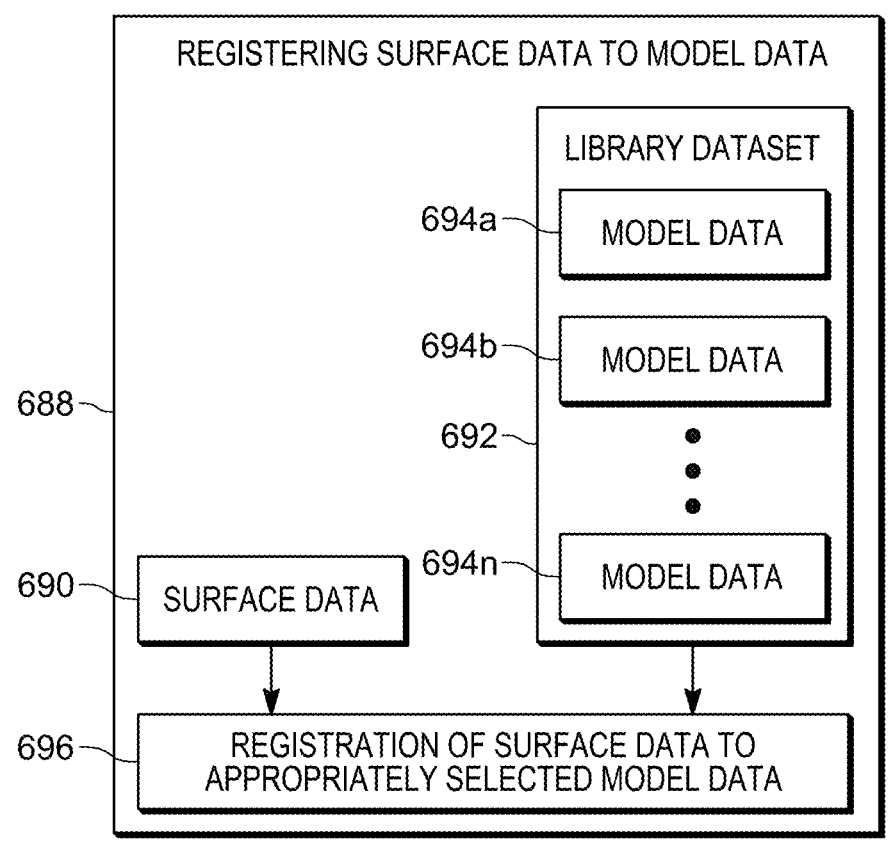
FIG. 11 illustrates a diagram that shows how surface data extracted from intra-oral imagery is fitted to model data maintained as a library dataset.

FIG. 11 illustrates a diagram 688 that shows how surface data 690 extracted from intra-oral imagery is fitted to one or more of model data 694 *a*, 694 *b*, . . . 694 *n* maintained as a library dataset 692. The library dataset 692 may include model data for various types of teeth (e.g., incisors, canines, molars, etc.) and also model data for various patient parameters, such as those based on age, gender, ethnicity, etc. In certain embodiments where the CBCT imagery is unavailable, the surface data 690 may be registered (reference numeral 696) to an appropriately selected model data 694 *a* . . . 694 *n* to provide better quality information to a dental practitioner. When the roots of a tooth are well formed and the crowns are relatively regular, then such fusion with model data is often adequate for treatment purposes. However, with as little as two to three degrees of error in alignment, such embodiments may have to be substituted with embodiments in which surface data from intra-oral imagery is registered with CBCT imagery to provide better quality information to the dental practitioner. In certain additional embodiments, the surface data is registered with the CBCT imagery with additional cues obtained from the model data.

Figure 12:
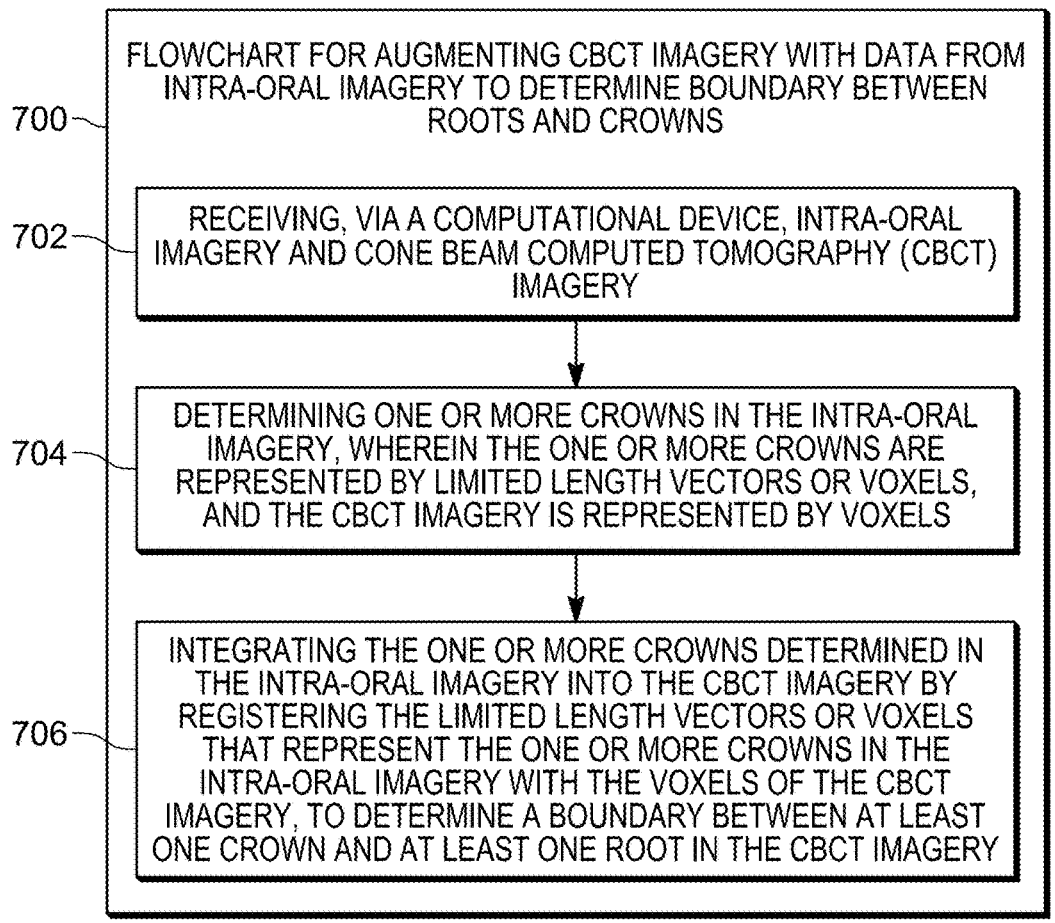
FIG. 12 illustrates a flowchart for augmenting CBCT imagery with data from intra-oral imagery to determine boundary between roots and crowns, in accordance with certain embodiments.

FIG. 12 illustrates a flowchart 700 for augmenting CBCT imagery with data from intra-oral imagery to determine the boundary between roots and crowns, in accordance with certain embodiments. The operations shown in flowchart 700 may be performed via the integrating application 108 that executes in the computational device 102.

Control starts at block 702 in which the computational device 102 receives intra-oral imagery 104 and CBCT imagery 106. The integrating application 108 determines (at block 704) one or more crowns in the intra-oral imagery, wherein the one or more crowns of the intra-oral imagery are represented by limited length vectors or voxels, and the CBCT imagery is represented by voxels. Control proceeds to block 706, in which the integrating application 108 integrates the one or more crowns determined in the intra-oral imagery into the CBCT imagery by registering the limited length vectors or voxels that represent the one or more crowns in the intra-oral imagery with the voxels of the CBCT imagery, to determine a boundary between at least one crown and at least one root in the CBCT imagery.

Figure 13:
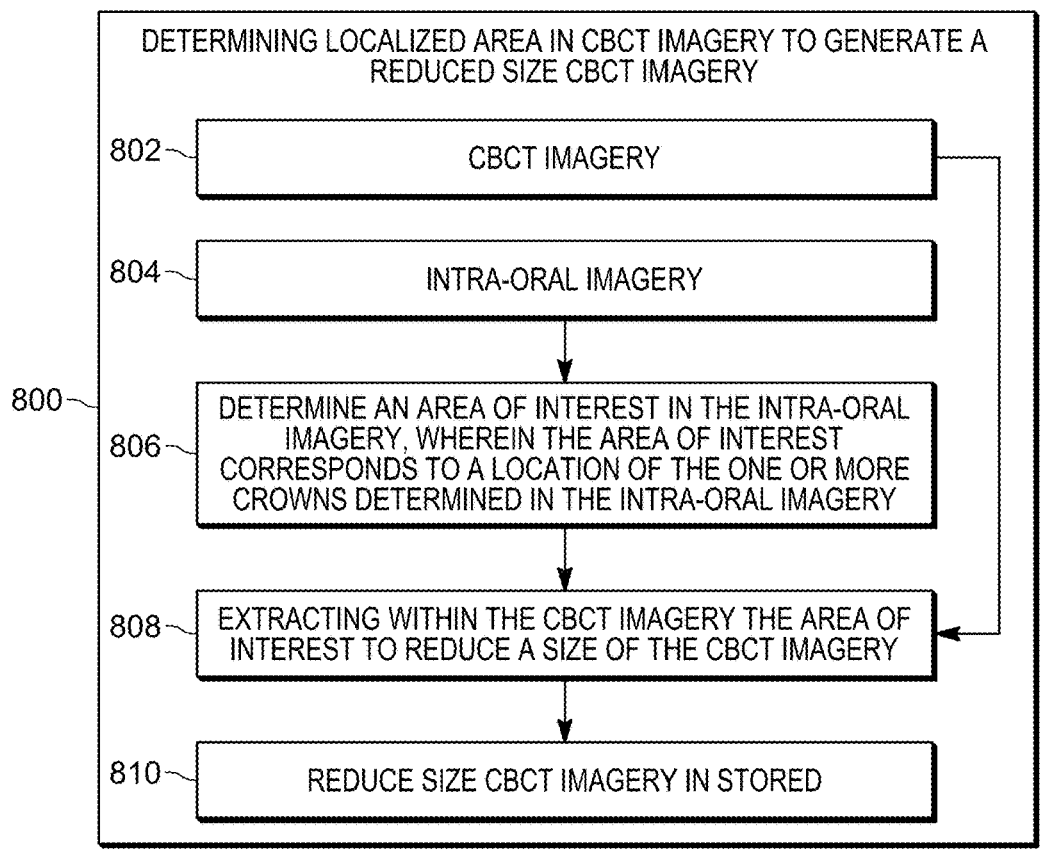
FIG. 13 illustrates a flowchart for determining a localized area in CBCT imagery to generate a reduced size CBCT imagery, by augmenting CBCT imagery with data from intra-oral imagery, in accordance with certain embodiments.

FIG. 13 illustrates a flowchart 800 for determining a localized area in CBCT imagery to generate a reduced size CBCT imagery, by augmenting CBCT imagery with data from intra-oral imagery, in accordance with certain embodiments. The operations shown in flowchart 800 may be performed via the integrating application 108 that executes in the computational device 102.

Control starts at blocks 802 and 804 in which CBCT imagery and intra-oral imagery are provided to the integrating application 108. The integrating application 108 determines (at block 806) an area of interest in the intra-oral imagery, wherein the area of interest corresponds to a location of the one or more crowns determined in the intra-oral imagery via segmentation.

Control proceeds to block 808 in which the integrating application 108 extracts from the CBCT imagery the area of interest to reduce the size of the CBCT imagery, and the reduced size CBCT imagery is stored (at block 810) in the computational device 102.

Therefore FIG. 8 illustrates certain embodiments in which the size of CBCT imagery is reduced by incorporating an area of interest determined from intra-oral imagery.

Figure 14:
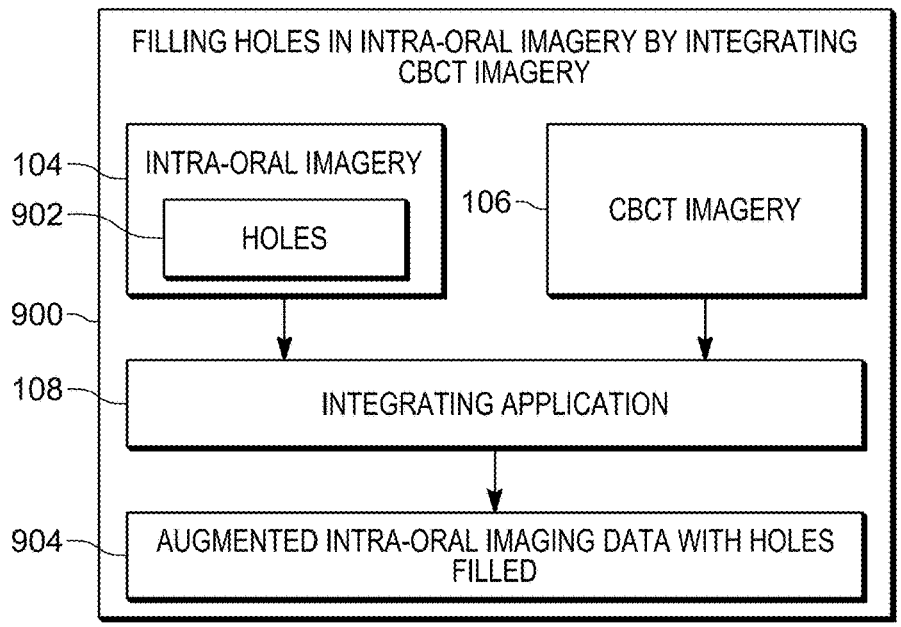
FIG. 14 illustrates a diagram that shows how holes are filled in intra-oral imagery by integrating CBCT imagery with intra-oral imagery, in accordance with certain embodiments.

FIG. 14 illustrates a diagram 900 that shows how holes are filled in intra-oral imagery by integrating CBCT imagery with intra-oral imagery, accordance with certain embodiments.

In FIG. 9 an exemplary intra-oral imagery 104 has holes 902 (i.e., areas of the crown of teeth that are not imaged by the intra-oral imaging system 112). The integrating application 108 uses the CBCT imagery 106 to fill the holes via the low precision crowns without holes that are found in the CBCT imagery 106, to generate augmented intra-oral imaging data 904 in which all holes are filled. In certain embodiments, a range of radiodensities are determined in voxels of a determined boundary between roots and crowns, and based on the range of radiodensities and the determined boundary, the holes in the intra-oral imagery are filled from selected voxels of the CBCT imagery.

Figure 15:
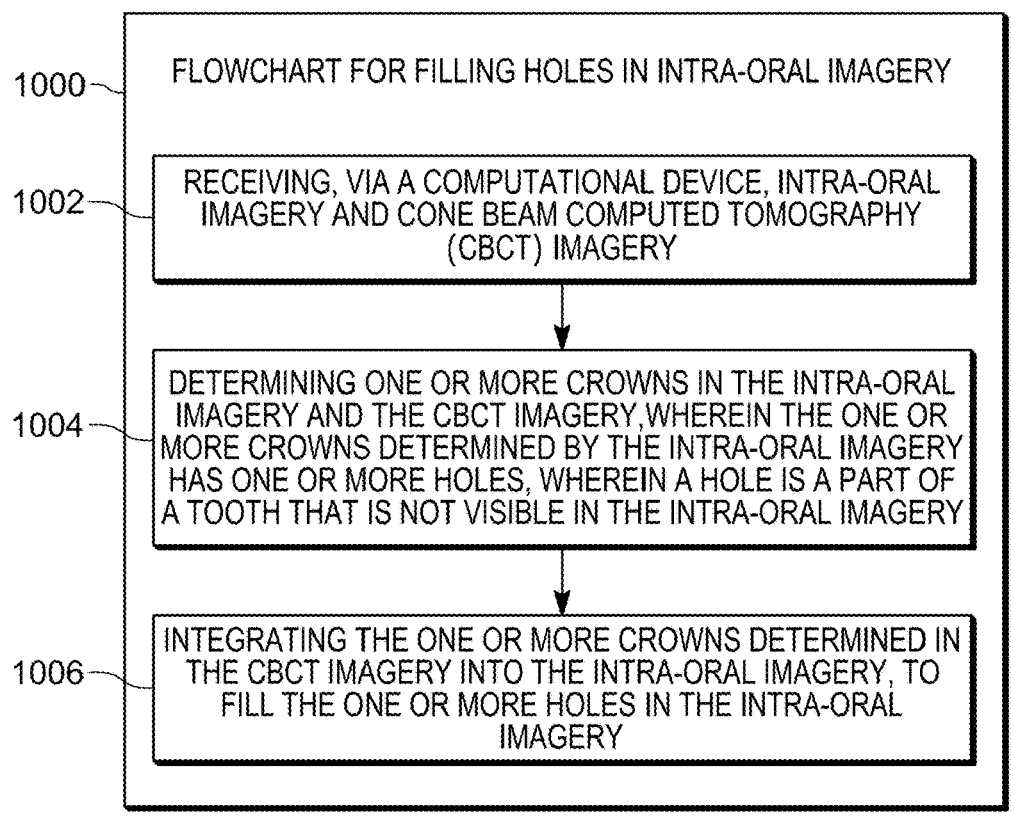
FIG. 15 illustrates a flowchart that shows how holes are filled in intra-oral imagery by integrating CBCT imagery with intra-oral imagery, in accordance with certain embodiments.

FIG. 15 illustrates a flowchart 1000 that shows how holes are filled in intra-oral imagery by integrating CBCT imagery with intra-oral imagery, accordance with certain embodiments. The operations shown in flowchart 1000 may be performed via the integrating application 108 that executes in the computational device 102.

Control starts at block 1002 in which the computational device 102 receives intra-oral imagery 104 and volumetric imagery, such as, cone beam computed tomography (CBCT) imagery 106. Control proceeds to block 1004, in which the integrating application 108 determines one or more crowns in the intra-oral imagery 104 and the CBCT imagery 106, where the one or more crowns determined by the intra-oral imagery 104 has one or more holes, and where a hole is a part of a tooth that is not visible in the intra-oral imagery. The one or more crowns determined in the CBCT imagery are integrated (at block 1006) into the intra-oral imagery 104, to fill the one or more holes in the intra-oral imagery.

Therefore FIGS. 14 and 15 illustrate how holes are filled in intra-oral imagery by integrating information from CBCT imagery. Conversely, if missing or degraded data is found in volumetric imagery, such missing or degraded data may be filled from surface data found in the intra-oral imagery.

Figure 16:
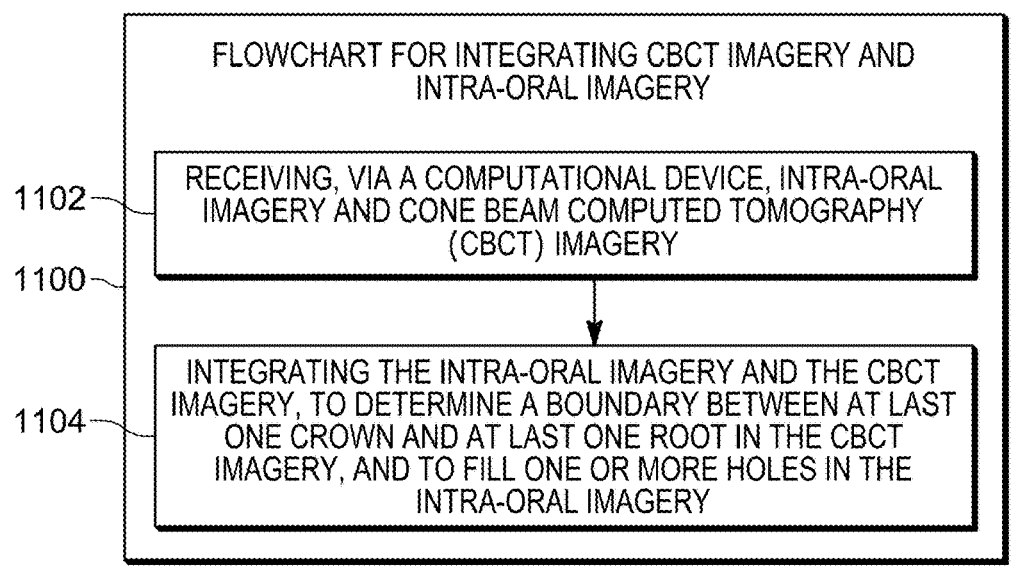
FIG. 16 illustrates a flowchart that shows how CBCT imagery is integrated with intra-oral imagery, in accordance with certain embodiments.

FIG. 16 illustrates a flowchart 1100 that shows how CBCT imagery 106 is integrated with intra-oral imagery 104, in accordance with certain embodiments. The operations shown in flowchart 1100 may be performed via the integrating application 108 that executes in the computational device 102.

Control starts at block 1102 in which a computational device 102 receives intra-oral imagery 104 and CBCT imagery 106. The intra-oral imagery 104 and the CBCT imagery 106 are integrated (at block 1104), to determine a boundary between at least one crown and at least one root in the CBCT imagery 106, and to fill one or more holes in the intra-oral imagery 104.

Figure 17:
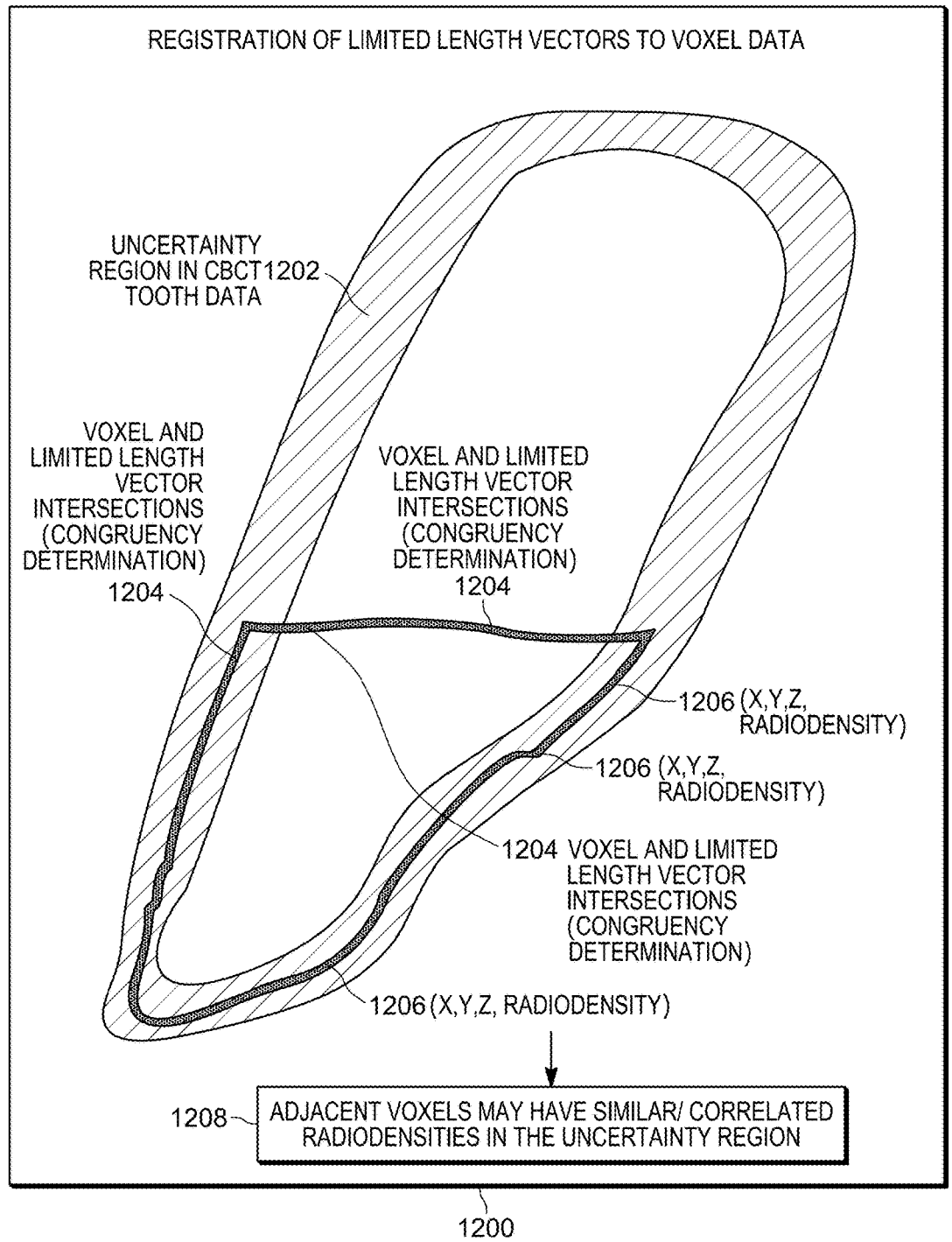
FIG. 17 illustrates a block diagram that shows how limited length vectors of intra-oral imagery are registered to voxel data of CBCT imagery, in accordance with certain embodiments.

FIG. 17 illustrates a block diagram 1200 that shows how limited length vectors of intra-oral imagery are registered to voxel data of CBCT or other volumetric imagery, in accordance with certain embodiments.

In FIG. 17 the hatched area indicated via reference numeral 1202 indicates an uncertainty region of the CBCT imagery in which the actual tooth boundary of the patient is likely to found. The limited length vectors (or voxels) of the intra-oral imagery are registered to the voxels of the CBCT imagery to determine the intersections 1204. At each of the intersections 1204 there is an X,Y,Z coordinate and an associated radiodensity (shown via reference numeral 1206), where adjacent voxels may have similar radiodensities or correlated radiodensities in the uncertainty region 1202 (as shown via reference numeral 1208).

Figure 18:
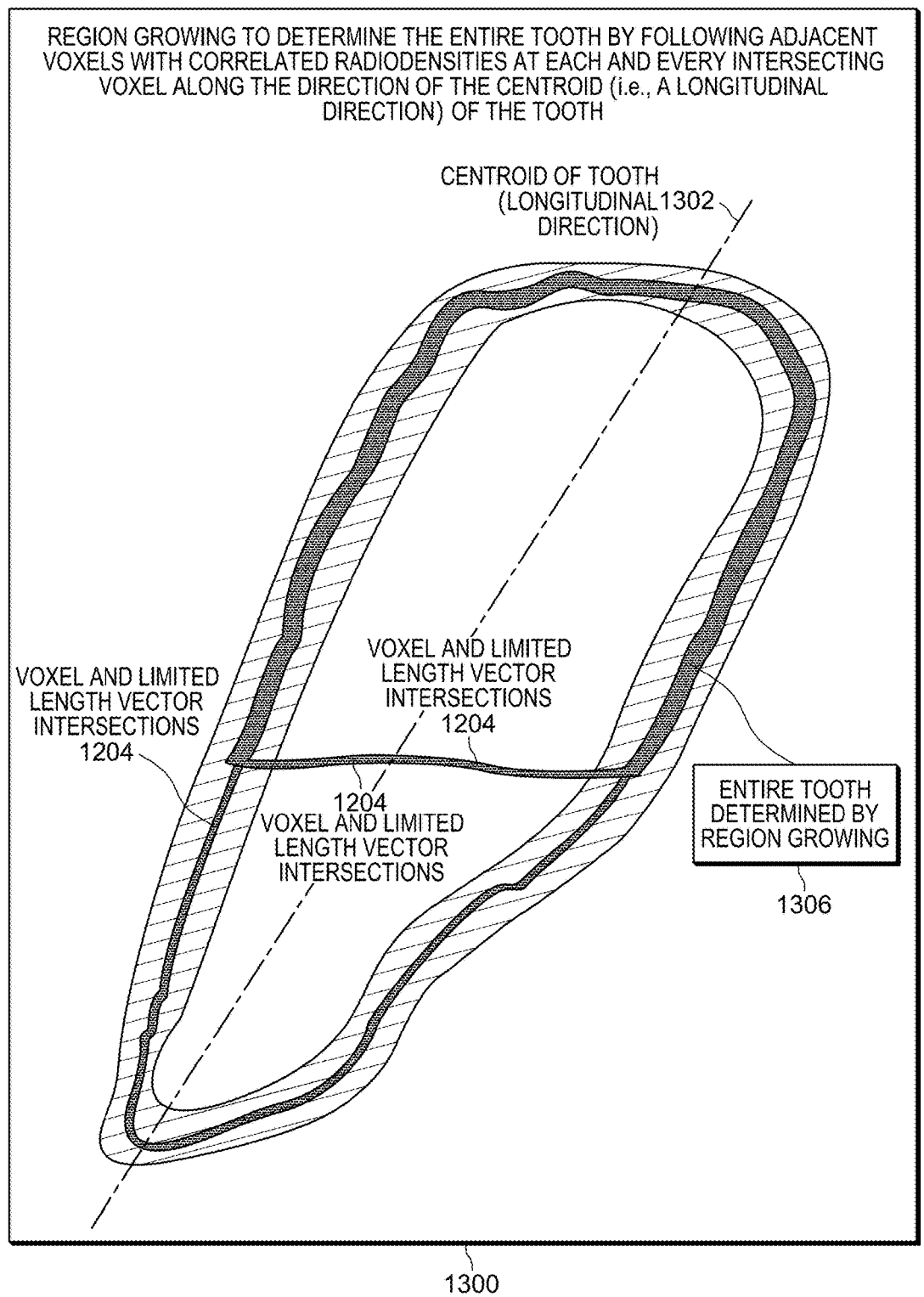
FIG. 18 illustrates a block diagram that shows how region growing is performed to determine the entire tooth by following adjacent voxels with correlated radiodensities at each and every intersecting voxel along the direction of the centroid or any other longitudinal direction of a tooth, in accordance with certain embodiments.

FIG. 18 illustrates a block diagram 1300 that shows how region growing is performed to determine the entire tooth by following adjacent voxels with correlated radiodensities at each and every intersecting voxel along the direction of the centroid 1302 of a tooth, in accordance with certain embodiments. The centroid is located along a longitudinal direction of the tooth. The correlated radiodensities may be determined via correlation windows of different sizes. For example, a cube of voxels with length, breadth, and height of three voxels each may be used as a correlation window to determine which adjacent voxel is most correlated to a previously determined voxel in terms of radiodensities.

Reference numeral 1306 shows the entire tooth outlined via region growing with seed values starting from the voxels and limited length vector (or surface voxel) intersections 1204 and the associated radiodensities. Other mechanisms may also be adopted for region growing to determine the entire tooth.

Figure 19:
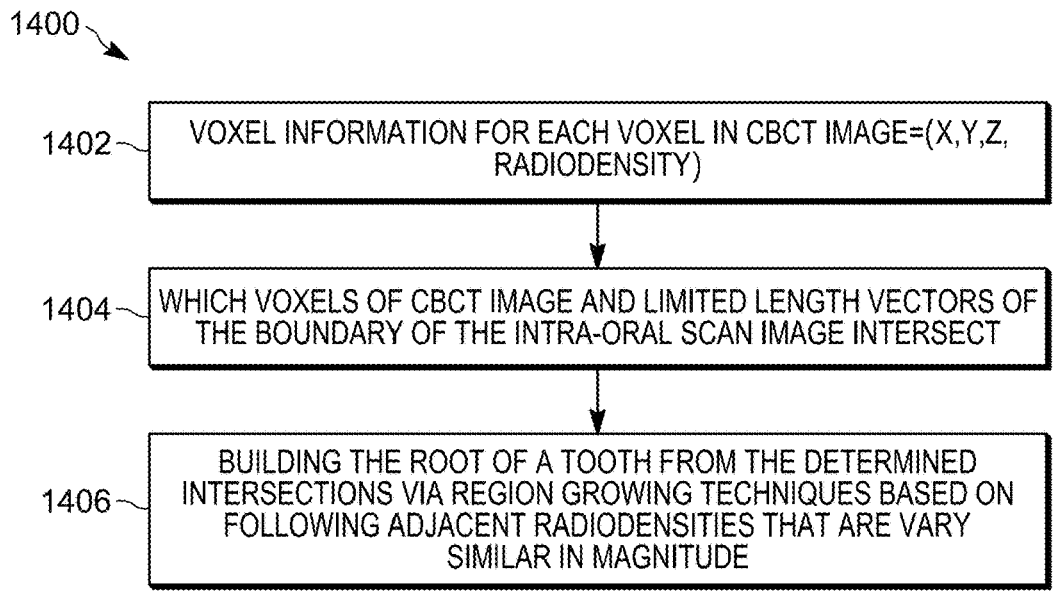
FIG. 19 illustrates a flowchart that shows how the root of a tooth is built from intersections of limited length vectors and voxels and region growing, in accordance with certain embodiments.

FIG. 19 illustrates a flowchart 1400 that shows how the root of a tooth is built from intersections of limited length vectors (or surface voxel) and voxels and region growing, in accordance with certain embodiments. Control starts at block 1402 where the voxel information at each voxel of a CBCT image is given by a volumetric coordinate X,Y,Z and the radiodensity. Control proceeds to block 1404 in which a determination is made as to which voxels of CBCT image and limited length vectors (or voxel) of the boundary of the crown of intra-oral image intersect. The root of the tooth is built (at block 1406) from the determined intersections via region growing techniques based on following adjacent radiodensities that are correlated (i.e., similar in magnitude) to each other.

Figure 20:
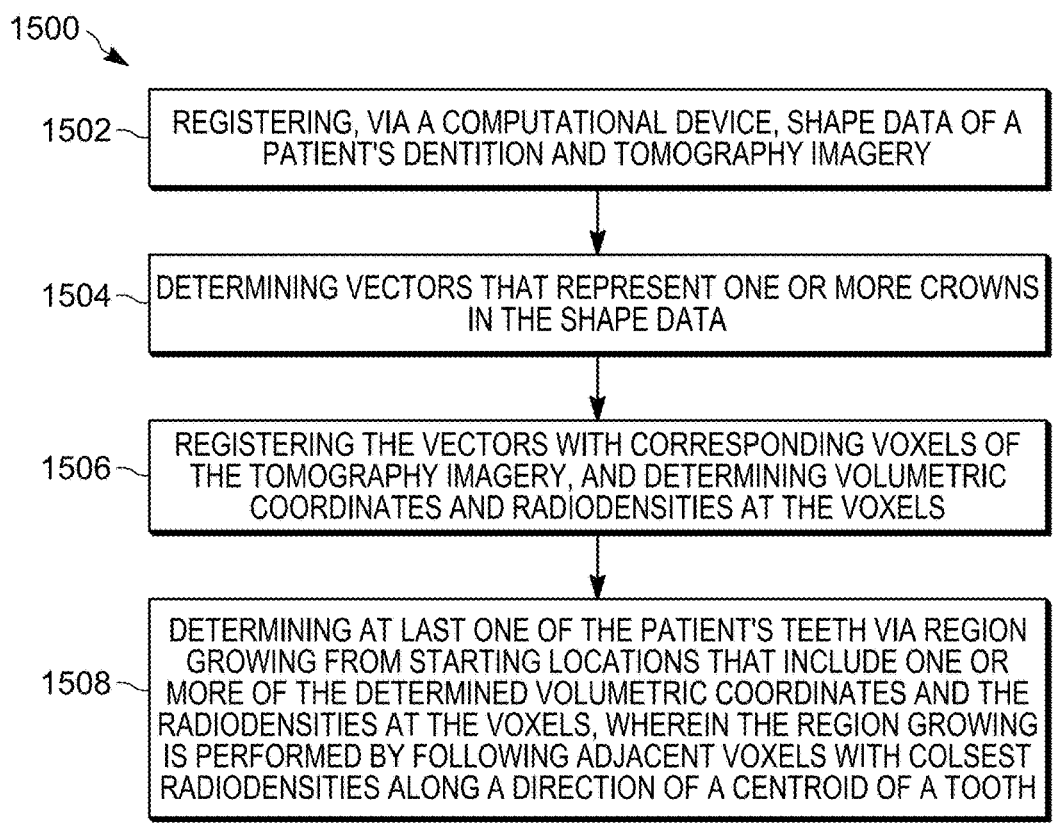
FIG. 20 illustrates a flowchart that shows how voxels of tomography imagery and limited length vectors of shape data are integrated, in accordance with certain embodiments.

FIG. 20 illustrates a flowchart 1500 that shows how voxels of tomography (i.e. volumetric) imagery and limited length vectors of shape data are integrated, in accordance with certain embodiments. A computational device receives (at block 1502) shape data of a patient's dentition and tomography imagery. Vectors that represent one or more crowns in the shape data are determined (at block 1504). The vectors are registered with corresponding voxels of the tomography imagery, and volumetric coordinates and radiodensities at the voxels are determined (at block 1506). At least one of the patient's teeth is determined via region growing from starting locations that include one or more of the determined volumetric coordinates and the radiodensities at the voxels, and the region growing is performed by following adjacent voxels with closest radiodensities along a direction of a centroid of a tooth (at block 1508). In alternative embodiments voxels (referred to as surface voxel) corresponding to the limited length vectors of the surface data may be used instead of the limited length vectors for registration.

Figure 21:
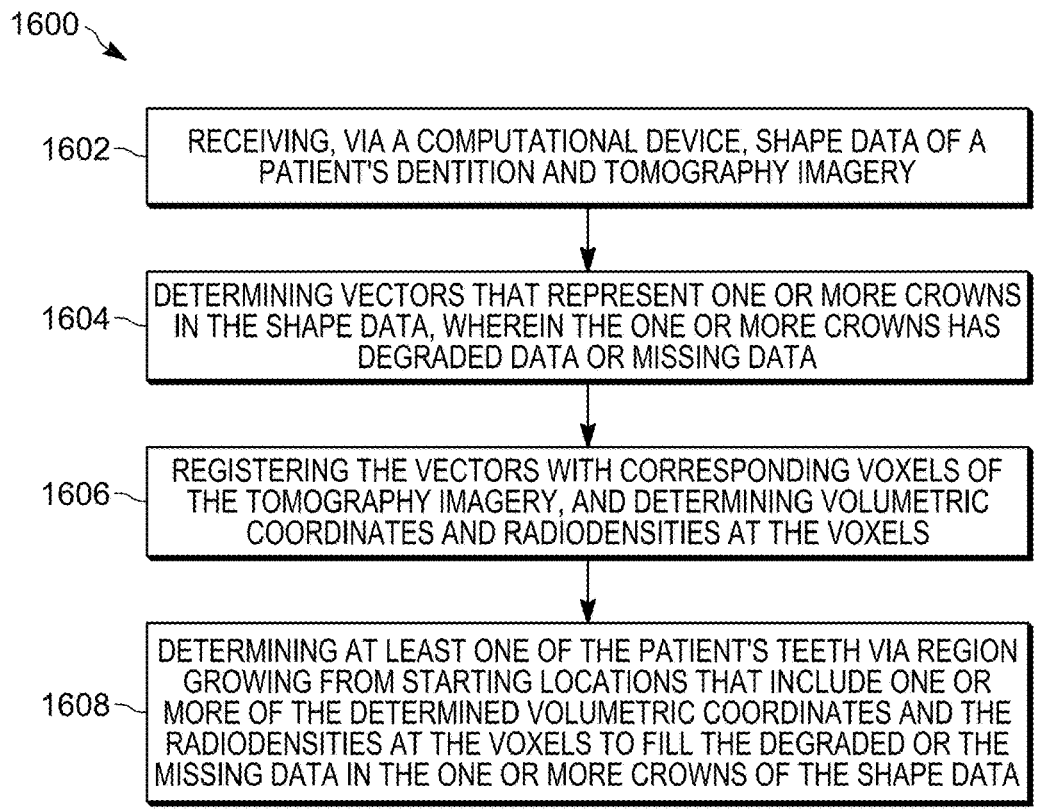
FIG. 21 illustrates a flowchart that shows how missing or degraded data in shape data is filled by integrating voxels of tomography imagery and limited length vectors of shape data, in accordance with certain embodiments.

FIG. 21 illustrates a flowchart 1600 that shows how missing or degraded data in shape data is filled by integrating voxels of tomography imagery and limited length vectors of shape data, in accordance with certain embodiments. A computational device receives (at block 1602) shape data of a patient's dentition and tomography imagery. Vectors that represent one or more crowns in the shape data are determined, wherein the one or more crowns has degraded data or missing data (at block 1604). The vectors are registered with corresponding voxels of the tomography imagery, and volumetric coordinates and radiodensities at the voxels are determined (at block 1606). At least one of the patient's teeth is determined via region growing from starting locations that include one or more of the determined volumetric coordinates and the radiodensities at the voxels to fill the degraded or the missing data in the one or more crowns of the shape data (at block 1606).

In certain alternative embodiments vectors are registered with corresponding voxels of the tomography imagery to determine volumetric coordinates and radiodensities at the voxels, to determine a tooth with greater precision and to fill missing or degraded data in the shape data. In certain embodiments, by determining the tooth with greater precision the received tomography imagery is obtained with usage of lesser radiation.

Figure 22:
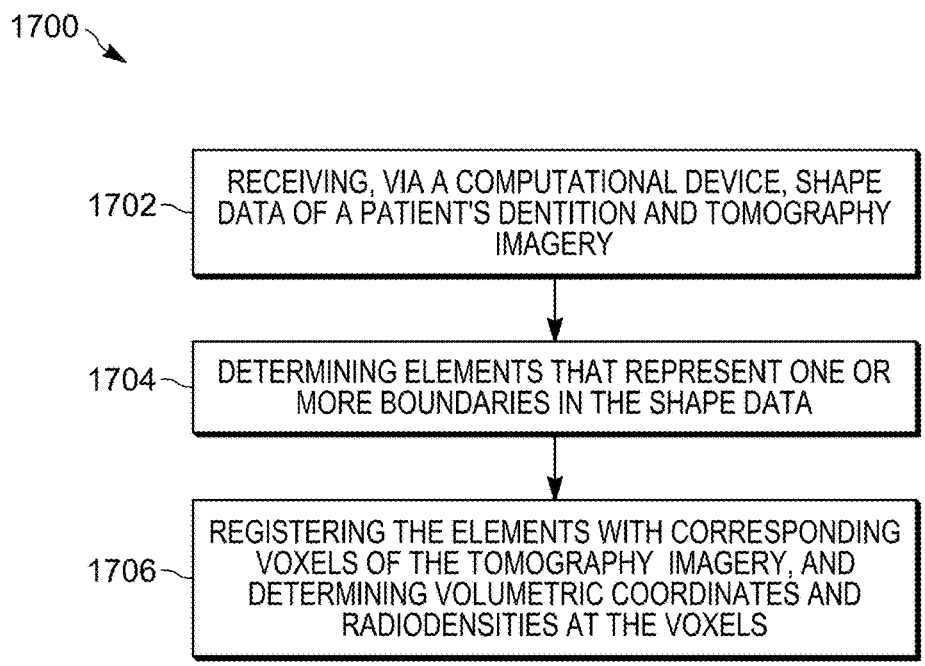
FIG. 22 illustrates a flowchart that shows registration of elements in shape data with corresponding voxels in tomographic imagery to determine volumetric coordinates and radiodensities at the voxels, in accordance with certain embodiments.

FIG. 22 illustrates a flowchart 1700 that shows registration of elements (e.g., vectors) in shape data with corresponding voxels in tomographic imagery to determine volumetric coordinates and radiodensities at the voxels, in accordance with certain embodiments. A computational device receives (at block 1702) shape data of a patient's dentition and tomography imagery. Elements (e.g. vectors or voxels) that represent one or more boundaries in the shape data are determined (at block 1704). The elements are registered with corresponding voxels of the tomography imagery, and volumetric coordinates and radiodensities at the voxels are determined (at block 1706). In certain embodiments, the boundaries in the shape data delineate one or more crowns of teeth.

FIG. 23 illustrates a flowchart 2300 that shows registration of elements in shape data of a patient's crown with corresponding voxels in volumetric imagery, in accordance with certain embodiments.

Control starts at block 2302 in which shape data of a patient's crown and volumetric imagery of the patient's tooth is received. A determination is made (at block 2304) of elements that represent one or more crowns in the shape data. A computational device is used to register (at block 2306) the elements with corresponding voxels of the volumetric imagery.

FIG. 24 illustrates a flowchart 2400 that shows registration of elements in shape data of a patient's crown with corresponding voxels in volumetric imagery to determine tooth shape, in accordance with certain embodiments.

Control starts at block 2402 in which shape data of a patient's crown and volumetric imagery are received. A determination is made (at block 2404) of elements that represent one or more crowns in the shape data. The elements are registered (at block 2406) with corresponding voxels of the volumetric imagery by using a computational device, and volumetric coordinates and radiodensities are determined to determine a tooth shape.

Therefore, FIGS. 1-24 illustrate certain embodiments in which the tooth of a patient is determined more accurately by integrating information extracted from intra-oral imagery and CBCT imagery. Also, degraded or missing data in the crowns of intra-oral imagery are filled by integrating information extracted from CBCT imagery. By integrating intra-oral imagery with CBCT imagery, both intra-oral imagery and CBCT imagery are enhanced to have greater functionalities and CBCT imagery may be obtained with usage of a lower amount of radiation.

Further Details of Embodiments

In a volumetric data representation there may be areas of high contrast and low contrast. When segmenting via thresholding (e.g., by thresholding radiodensities) it may be easier to threshold crowns than roots. This is because crowns appear with high density against soft tissue. It may be noted that roots appear with low contrast against the bone. High contrast junctions may be easier to segment this manner. In certain embodiments, the crowns may be thresholded and the borders may be used to seed the segmentation to isolate the roots. Thus the volumetric data set may be used to segment itself. This may automatically register the crown root object. This may even be used to register the crown surface data.

In certain embodiments, instead of segmenting roots, certain embodiments may extract only the centroid of the root.

Certain embodiments may link the shape and tomography imagery data together in a file system. For example, information may be added to the headers of the image files of both the CBCT and intra-oral scan data to enable viewing software to easily reference one from the other. Alternatively, the viewing software may keep track of which intra-oral scan image and CBCT image files have been registered with one another and store the information in a separate file. In certain embodiments correlation or optimization techniques may be used to find the intersection points in the image data.

In certain embodiments, the output of the processes is a data structure that is an advanced representation of the surface or a volumetric data enhanced by the fusion process of registration of multiple sources of imagery. Multidimensional data representation and visualization techniques may be used to display such enhanced surfaces or volumes. In certain embodiments, the collected image data may after processing and registration be rendered and displayed as three dimensional objects via volumetric rendering and segmentation.

Additional Details of Embodiments

The operations described in the figures may be implemented as a method, apparatus or computer program product using techniques to produce software, firmware, hardware, or any combination thereof. Additionally, certain embodiments may take the form of a computer program product embodied in one or more computer readable storage medium(s) having computer readable program code embodied therein.

A computer readable storage medium may include an electronic, magnetic, optical, electromagnetic, or semiconductor system, apparatus, or device, or any suitable combination of the foregoing. The computer readable storage medium may also comprise an electrical connection having one or more wires, a portable computer diskette or disk, a hard disk, a random access memory (RAM), a read-only memory (ROM), an erasable programmable read-only memory (EPROM or Flash memory), a portable compact disc read-only memory (CD-ROM), an optical storage device, a magnetic storage device, etc. A computer readable storage medium may be any tangible medium that can contain, or store a program for use by or in connection with an instruction execution system, apparatus, or device.

Computer program code for carrying out operations for aspects of the present invention may be written in any combination of one or more programming languages. Aspects of the present invention are described below with reference to flowchart illustrations and/or block diagrams of methods, system and computer program products according to certain embodiments. At least certain operations that may have been illustrated in the figures show certain events occurring in a certain order. In alternative embodiments, certain operations may be performed in a different order, modified or removed. Additionally, operations may be added to the above described logic and still conform to the described embodiments. Further, operations described herein may occur sequentially or certain operations may be processed in parallel. Yet further, operations may be performed by a single processing unit or by distributed processing units. Computer program instructions can implement the blocks of the flowchart. These computer program instructions may be provided to a processor of a computer for execution.

Figure 25:
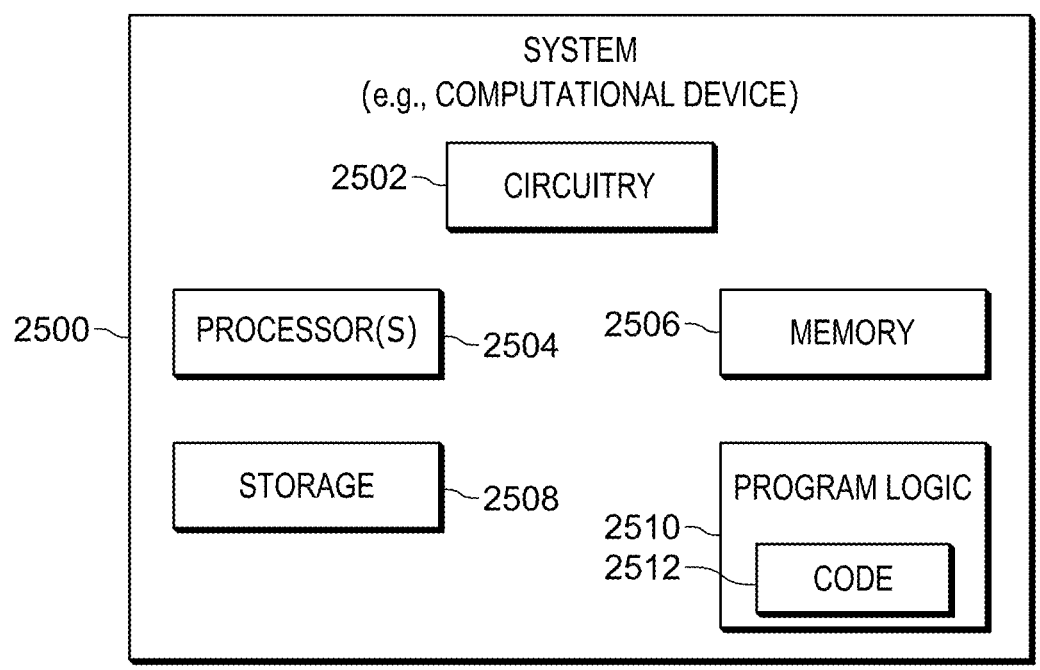
FIG. 25 illustrates a block diagram of a computational device that shows certain elements of the computational device shown in FIG. 1, in accordance with certain embodiments.

FIG. 25 illustrates a block diagram that shows certain elements that may be included in the computational device 102, in accordance with certain embodiments. The system 2500 may comprise the computational device 102 and may include a circuitry 2502 that may in certain embodiments include at least a processor 2504. The system 2500 may also include a memory 2506 (e.g., a volatile memory device), and storage 2508. The storage 2508 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 2508 may comprise an internal storage device, an attached storage device and/or a network accessible storage device. The system 2500 may include a program logic 2510 including code 2512 that may be loaded into the memory 2506 and executed by the processor 2504 or circuitry 2502. In certain embodiments, the program logic 2510 including code 2512 may be stored in the storage 2508. In certain other embodiments, the program logic 2510 may be implemented in the circuitry 2502. Therefore, while FIG. 25 shows the program logic 2510 separately from the other elements, the program logic 2510 may be implemented in the memory 2506 and/or the circuitry 2502.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method comprising:
receiving, by a computer, shape data of a super-gingival portion of a patient's first tooth;
receiving, by the computer, volumetric imagery of the super-gingival portion of the first tooth and volumetric imagery of a sub-gingival portion of the first tooth;
registering the shape data of the super-gingival portion with the volumetric data of the super-gingival portion to obtain a registration result using the computer;
determining, by the computer, at least one criterion for detecting a surface of the first tooth in the volumetric imagery of the super-gingival or the sub-gingival portions using the registration result; and
detecting, by the computer, a surface of the sub-gingival portion of the first tooth within the volumetric imagery of the sub-gingival portion of the first tooth using the at least one criterion,
wherein determining the at least one criterion includes determining coordinate information for the volumetric imagery registered with shape data corresponding to the super-gingival portion of the first tooth, and
wherein detecting a surface of the sub-gingival portion of the first tooth within the volumetric imagery includes identifying a portion of the volumetric imagery corresponding to the sub-gingival portion of the first tooth that is adjacent to a portion of the volumetric imagery registered with the shape data corresponding to the super-gingival portion of the first tooth using the coordinate information.

2. The method of claim 1, further comprising:
receiving, by the computer, shape data of super-gingival portions of a plurality of teeth;
receiving, by the computer, volumetric imagery of super-gingival and sub-gingival portions of the plurality of teeth; and
determining, by the computer, elements that represent the super-gingival portions of the plurality of teeth within the shape data.

3. The method of claim 2, further comprising:
registering, by the computer, the shape data of the super-gingival portions of the plurality of teeth with the volumetric data of the super-gingival portions of the plurality of teeth to obtain the registration result; and
detecting, by the computer, surfaces of the sub-gingival portions of the plurality of teeth within the volumetric imagery of the sub-gingival portions of the plurality of teeth using the at least one criterion.

4. The method of claim 1, wherein determining at least one criterion for detecting a surface of the first tooth in the volumetric imagery includes determining radiodensities corresponding to portions of the volumetric imagery registered with the shape data.

5. The method of claim 4, wherein detecting a surface of the sub-gingival portion of the first tooth includes identifying adjacent portions that possess correlated radiodensities along a longitudinal direction of the patient's first tooth.

6. The method of claim 5, wherein detecting a surface of the sub-gingival portion of the first tooth within the volumetric imagery includes
comparing a radiodensity of the first portion of the volumetric imagery to a radiodensity of a second portion of the volumetric imagery.

7. The method of claim 1, further comprising capturing the volumetric imagery using an imaging modality selected from a group consisting of tomographic imagery, ultrasonic imagery, cone beam computed tomography, and magnetic resonance imagery.

8. A dental imaging system for identifying a sub-gingival surface of a tooth in volumetric imagery data, the dental imaging system including a processor and a memory, the memory storing instructions that, when executed by the processor, cause the dental imaging system to:
receive shape data of a super-gingival portion of a patient's first tooth;
receive volumetric imagery data of the super-gingival portion of the first tooth and volumetric imagery data of a sub-gingival portion of the first tooth;
register the shape data of the super-gingival portion with the volumetric imagery data of the super-gingival portion to obtain a registration result;
determine at least one criterion for detecting a surface of the first tooth in the volumetric imagery data of the super-gingival or the sub-gingival portions using the registration result; and
detect a surface of the sub-gingival portion of the first tooth within the volumetric imagery data of the sub-gingival portion of the first tooth using the at least one criterion,
wherein the instructions, when executed by the processor, cause the dental imaging system to determine the at least one criterion by determining coordinate information for portions of the volumetric imagery registered with shape data corresponding to the super-gingival portion of the first tooth, and to detect the surface of the sub-gingival portion of the first tooth within the volumetric imagery by identifying a portion in the volumetric imagery corresponding to the sub-gingival portion of the first tooth that is adjacent to a portion of the volumetric imagery registered with the shape data corresponding to the super-gingival portion of the first tooth using the coordinate information.

9. The dental imaging system of claim 8, wherein the instructions, when executed by the processor, further cause the dental imaging system to:
receive shape data of super-gingival portions of a plurality of teeth;
receive volumetric imagery data of super-gingival and sub-gingival portions of the plurality of teeth; and
determine elements that represent the super-gingival portions of the plurality of teeth within the shape data.

10. The dental imaging system of claim 9, wherein the instructions, when executed by the processor, further cause the dental imaging system to:
register the shape data of the super-gingival portions of the plurality of teeth with the volumetric imagery data of the super-gingival portions of the plurality of teeth to obtain the registration result; and
detect surfaces of the sub-gingival portions of the plurality of teeth within the volumetric imagery data of the sub-gingival portions of the plurality of teeth using the at least one criterion.

11. The dental imaging system of claim 8, wherein the instructions, when executed by the processor, cause the dental imaging system to determine the at least one criterion for detecting the surface of the first tooth in the volumetric imagery data by determining radiodensities corresponding to portions of the volumetric imagery data registered with the shape data.

12. The dental imaging system of claim 11, wherein the instructions, when executed by the processor, cause the dental imaging system to detect the surface of the sub-gingival portion of the first tooth in the volumetric imagery data by identifying adjacent portions that possess correlated radiodensities along a longitudinal direction of the patient's first tooth.

13. The dental imaging system of claim 12, wherein the instructions, when executed by the processor, cause the dental imaging system to detect a surface of the sub-gingival portion of the first tooth within the volumetric imagery data by comparing a radiodensity of a first portion of the volumetric imagery to a radiodensity of a second portion of the volumetric imagery.

14. The dental imaging system of claim 8, further comprising an imaging device configured to capture the volumetric imagery data using an imaging modality selected from a group consisting of tomographic imagery, ultrasonic imagery, cone beam computed tomography, and magnetic resonance imagery, and
wherein the instructions, when executed by the processor, cause the dental imaging system to receive the volumetric imagery data by receiving the volumetric imagery from the imaging device.

15. A dental imaging system for identifying a sub-gingival surface of a tooth in volumetric imagery data, the dental imaging system comprising:
a surface scanner configured to capture shape data of a super-gingival portion of a patient's first tooth;
a volumetric imaging device configured to capture volumetric imagery data of the super-gingival portion of the first tooth and volumetric imagery data of a sub-gingival portion of the first tooth; and
a computer configured to
receive the shape data from the surface scanner,
receive the volumetric imagery data of the super-gingival portion of the first tooth and the volumetric imagery data of the sub-gingival portion of the first tooth from the volumetric imaging device,
register the shape data of the super-gingival portion with the volumetric imagery data of the super-gingival portion to obtain a registration result,
determine coordinate information for the volumetric imagery registered with shape data corresponding to the super-gingival portion of the first tooth, and
detect a surface of the sub-gingival portion of the first tooth within the volumetric imagery data of the sub-gingival portion of the first tooth by identifying a portion of the volumetric imagery corresponding to the sub-gingival portion of the first tooth that is adjacent to a portion of the volumetric imagery registered with the shape data corresponding to the super-gingival portion of the first tooth using the coordinate information.

\* \* \* \* \*